(12) United States Patent
Kitajima et al.

(10) Patent No.: US 7,727,158 B2
(45) Date of Patent: Jun. 1, 2010

(54) PULSE WAVE DATA ANALYZING METHOD, SYSTEM, AND PROGRAM PRODUCT

(75) Inventors: Kazumi Kitajima, Higashiosaka (JP);
Yoshiroh Nagai, Nishinomiya (JP);
Masatake Fukunami, Osaka (JP);
Yasumasa Tsukamoto, Osaka (JP)

(73) Assignee: Konica Minolta Sensing, Inc., Sakai-shi (JP)

( * ) Notice: Subject to any disclaimer, the term of this patent is extended or adjusted under 35 U.S.C. 154(b) by 764 days.

(21) Appl. No.: 11/544,050

(22) Filed: Oct. 5, 2006

(65) Prior Publication Data

US 2007/0123787 A1 May 31, 2007

(30) Foreign Application Priority Data

Oct. 6, 2005  (JP) ............................. 2005-293212
Aug. 21, 2006  (JP) ............................. 2006-224132

(51) Int. Cl.
*A61B 5/02* (2006.01)
(52) U.S. Cl. ...................... 600/500; 600/485; 600/509; 600/504; 600/502; 600/521
(58) Field of Classification Search ......... 600/500–503, 600/508–509, 516, 521
See application file for complete search history.

(56) References Cited

U.S. PATENT DOCUMENTS 6,095,984 A * 8/2000 Amano et al. ............... 600/500
6,161,038 A * 12/2000 Schookin et al. ............ 600/519
6,993,378 B2 * 1/2006 Wiederhold et al. ......... 600/509

FOREIGN PATENT DOCUMENTS

JP      2001-70265 A      3/2001

* cited by examiner

*Primary Examiner*—Robert L Nasser
*Assistant Examiner*—Michael D'Angelo
(74) *Attorney, Agent, or Firm*—Sidley Austin LLP

(57) ABSTRACT

There is provided a pulse wave data analyzing method for extracting vital information out of pulse wave data concerning a living body. The method comprises a noise removal step of: detecting bottom values and peak values along a time axis in a time-series manner out of pulse wave data obtained by sequentially measuring a pulse wave of a subject for a predetermined period; making pairs with respect to the bottom values and the peak values adjacent to each other on the time axis to obtain bottom-to-peak amplitude values along the time axis, the bottom-to-peak amplitude value being a difference between the bottom value and the peak value in each of the pairs; and comparing each set of the two bottom-to-peak amplitude values adjacent to each other along the time axis to remove the bottom value and the peak value relating to the smaller bottom-to-peak amplitude value in the each set as a noise, if a ratio of the one of the two bottom-to-peak amplitude values to the other one of the two bottom-to-peak amplitude values is larger than a predetermined value.

16 Claims, 20 Drawing Sheets

RAW PULSE WAVEFORM

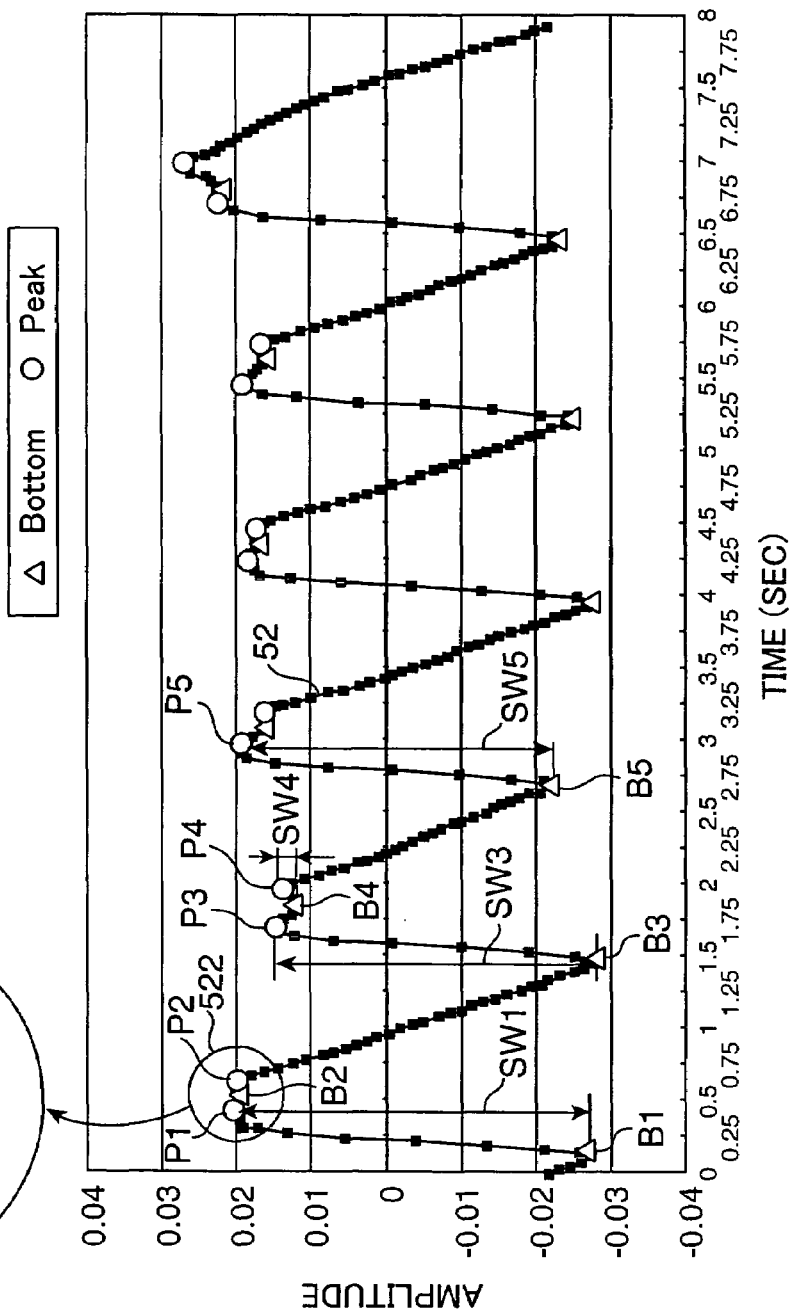
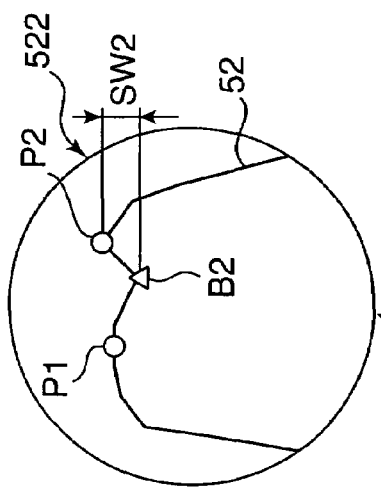
FIG.8 ulse wave analyzing method of detecting pulse wave RR intervals by calculating a speed pulse waveform based on first derivation of a pulse waveform detected by a pulse wave sensor, and by detecting peaks of the speed pulse waveform.

PULSE WAVE DATA ANALYZING METHOD, SYSTEM, AND PROGRAM PRODUCT

This application is based on Japanese Patent Application No. 2005-293212 filed on Oct. 6, 2005, and No. 2006-224132 filed on Aug. 21, 2006, respectively, the contents of which are hereby incorporated by reference.

BACKGROUND OF THE INVENTION

1. Field of the Invention

The present invention relates to a pulse wave data analyzing method, a system, and a program product for extracting information corresponding to electrocardiogram RR intervals out of pulse wave data concerning a living body.

2. Description of the Related Art

There is widely used, as an arrhythmia diagnostic method, a method of measuring an electrocardiogram of a subject, and using RR intervals in the electrocardiogram. The RR interval is a peak-to-peak interval of two consecutive R waves, which are the most frequently observed waves among P waves, Q waves, R waves, S waves, and T waves in one cycle of heartbeat in an electrocardiogram, as shown in FIG. 20. Expressing the RR intervals in a time-series manner enables to find out a heartbeat fluctuation. The heartbeat fluctuation is widely and clinically used as an index for assessing a biological control function of an autonomic nervous system involved in an organic activity of a living body.

The electrocardiogram measurement is generally performed, using a holter monitor equipped with electrodes for detecting cardiac activity potentials of a subject, or a like device. In use of the holter monitor, data measurement is conducted under a condition that after five or so electrodes are attached to the chest of the subject, and a data receiver is mounted on the waist of the subject in a medical institute, the subject performs a daily activity for one day or so. After the measurement is completed, the data stored in the receiver is outputted to a predetermined analyzer for an electrocardiographic waveform analysis to obtain the RR-intervals. The electrocardiogram measurement using the holter monitor requires the subject to perform a daily activity, with the electrodes being constantly attached to the body, which is stressful to the subject.

In view of the above, there is proposed a method of extracting information (hereinafter, called as "pulse wave RR intervals") corresponding to the RR intervals, out of pulse wave data, without relying on an electrocardiogram. The term "pulse wave" in the specification and claims of the application means a change in volume of an arterial vessel resulting from blood inflow, which is observed as a waveform through a body surface, and is a vasomotor response. The pulse wave is associated with cardiac movements. Measuring peripheral vascular movements of a living body enables to indirectly obtain information substantially equivalent to RR intervals obtained based on an electrocardiogram.

Concerning the pulse wave RR interval detection, a first conventional art discloses a pulse wave RR interval measuring device for calculating pulse wave RR intervals by detecting a pulse wave of a subject along a time axis by a pulse wave sensor, and by analyzing pulse wave data obtained by a calculator to obtain peak values and peak points of time. A second conventional art discloses an arrhythmia detector for detecting an accurate pulse wave component by frequency-analyzing a pulse waveform detected by a pulse waveform detector and by removing a body motion component, and for detecting an arrhythmia, using the obtained frequency analysis result. Furthermore, a third conventional art discloses a pulse wave analyzing method of detecting pulse wave RR intervals by calculating a speed pulse waveform based on first derivation of a pulse waveform detected by a pulse wave sensor, and by detecting peaks of the speed pulse waveform.

The peaks of the pulse wave data, however, are not sharp peaks generally observed in R waves of an electrocardiogram. Also, the pulse wave data includes notches, reflected wave components, or the like, which correspond to sites of a pulse waveform where relatively small peak portions and bottom portions appear. The notches, the reflected wave components, or the like become noises in peak detection. Hereinafter, the notches, the reflected wave components, or the like are simply called as "notches" to simplify the description. It is not easy to automatically detect peaks corresponding to the R waves based on raw pulse wave data according to the conventional art. The first and the second conventional art do not particularly mention an approach of accurately extracting peaks out of pulse wave data. The pulse wave analyzing method disclosed in the third conventional art is capable of removing the notches to some extent. However, since the third conventional art adopts a method of removing the notches, using a threshold value obtained based on a mean value of peak-to-peak intervals, the method may misjudge an actual peak as a noise in the case where appearance of a peak is unpredictable as in the case of an arrhythmia.

SUMMARY OF THE INVENTION

In view of the above problems residing in the conventional examples, it is an object of the present invention to provide a pulse wave data analyzing method, a system, and a program product that enable to accurately detect peaks and bottoms by securely removing notch portions included in pulse wave data, even if an arrhythmia or a like symptom has occurred in a subject, and to detect vital information e.g. information having a high correlation to RR-intervals obtained based on an electrocardiogram. Hereinafter, the information is sometimes called as "pulse wave peak-to-peak intervals" in light of obtaining peak-to-peak intervals or bottom-to-bottom intervals.

An aspect of the invention is directed to a pulse wave data analyzing method for extracting vital information out of pulse wave data concerning a living body. The method comprises a noise removal step of: detecting bottom values and peak values along a time axis in a time-series manner out of pulse wave data obtained by sequentially measuring a pulse wave of a subject for a predetermined period; making pairs with respect to the bottom values and the peak values adjacent to each other on the time axis to obtain bottom-to-peak amplitude values along the time axis, the bottom-to-peak amplitude value being a difference between the bottom value and the peak value in each of the pairs; and comparing each set of the two bottom-to-peak amplitude values adjacent to each other along the time axis to remove the bottom value and the peak value relating to the smaller bottom-to-peak amplitude value in the each set as a noise, if a ratio of the one of the two bottom-to-peak amplitude values to the other one of the two bottom-to-peak amplitude values is larger than a predetermined value.

These and other objects, features and advantages of the present invention will become more apparent upon reading the following detailed description along with the accompanying drawing.

BRIEF DESCRIPTION OF THE DRAWING

FIG. 8 is a graph showing a manner as to how bottom values, peak values, and bottom-to-peak amplitude values are detected out of the pulse waveform shown in FIG. 7.

DETAILED DESCRIPTION OF THE PREFERRED EMBODIMENTS

Figure 1:
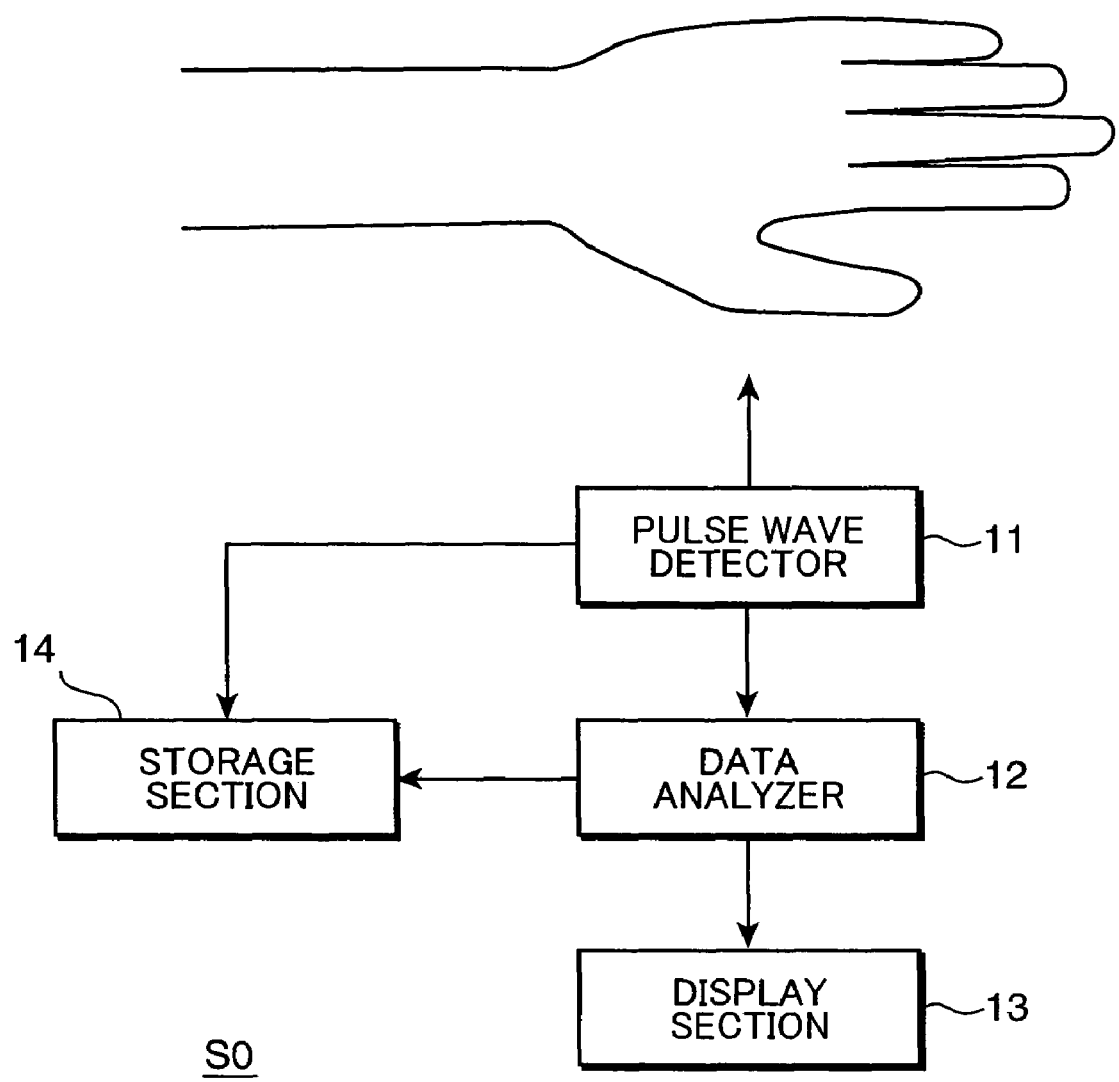
FIG. 1 is a block diagram schematically showing an entire configuration of a pulse wave data analyzing system according to an embodiment of the invention.

In the following, an embodiment of the invention is described referring to the drawings.

FIG. 1 is a block diagram schematically showing an entire configuration of a pulse wave data analyzing system "S0" embodying the invention. The pulse wave data analyzing system "S0" is a system capable of extracting information relating to pulse wave peak-to-peak intervals corresponding to RR-intervals in an electrocardiogram, out of pulse wave data concerning a subject i.e. a living body. The pulse wave data analyzing system "S0" includes a pulse wave detector 11, a data analyzer 12, a display section 13, and a storage section 14.

The pulse wave detector 11 obtains pulse wave information concerning a subject at a predetermined sampling frequency to acquire pulse wave data in association with a time axis i.e. data obtained by sequentially measuring a pulse wave of the subject for a predetermined period. Various pulse wave measuring methods are applicable in the embodiment. A preferred example of the method is a method utilizing light absorption characteristics of hemoglobin in blood. The method utilizes a phenomenon that in the case where light is irradiated onto a living body, the amount of reflected light from the living body or transmitted light through the living body is varied resulting from a pulse-like change of the amount of hemoglobin due to a pulsation of blood flow accompanied by a heartbeat of the living body, because hemoglobin in blood has a light absorption characteristic. In measurement, pulse wave data can be obtained by removably attaching a reflective or transmissive sensor equipped with a light emitter and a light detector onto a fingertip or a like portion of a subject, and by monitoring the amount of received light by the light detector. A photoplethysmographic sensor, a pulse oximeter capable of measuring a blood oxygen saturation, or a like device is a preferred example of the reflective or transmissive sensor. Alternatively, pulse wave data may be obtained by directly detecting a pulse pressure by a vascular pulsation, with use of a pressure sensor or a like device.

The data analyzer 12 includes an ROM (Read Only Memory) for storing various control programs or the like, an RAM (Random Access Memory) for temporarily storing data, a central processing unit (CPU) for reading out the various control programs or the like from the ROM for execution, and a DSP (Digital Signal Processor), and analyzes the pulse wave data obtained by the pulse wave detector 11. As will be described later in detail, the data analyzer 12 performs a noise removal process of removing notch noises included in the pulse wave data, and a process of obtaining peak-to-peak intervals or bottom-to-bottom intervals, which appear on a pulse waveform, based on the pulse wave data after the noise removal.

The display section 13 displays data processed by the data analyzer 12. Examples of the display section 13 are a liquid crystal display (LCD), a 7-segment LED display, an organic photo luminescent display, a CRT (Cathode Ray Tube), and a plasma display. Various measurement information such as data analysis results concerning the pulse wave data are displayed on the display section 13 in an intended format such as textual information, image information, or lighting information, according to needs.

The storage section 14 temporarily stores therein the pulse wave data obtained by the pulse wave detector 11, the data analysis results obtained by the data analyzer 12, or the like. Examples of the storage section 14 are an RAM and an EPROM (Erasable and Programmable ROM).

Figure 2:
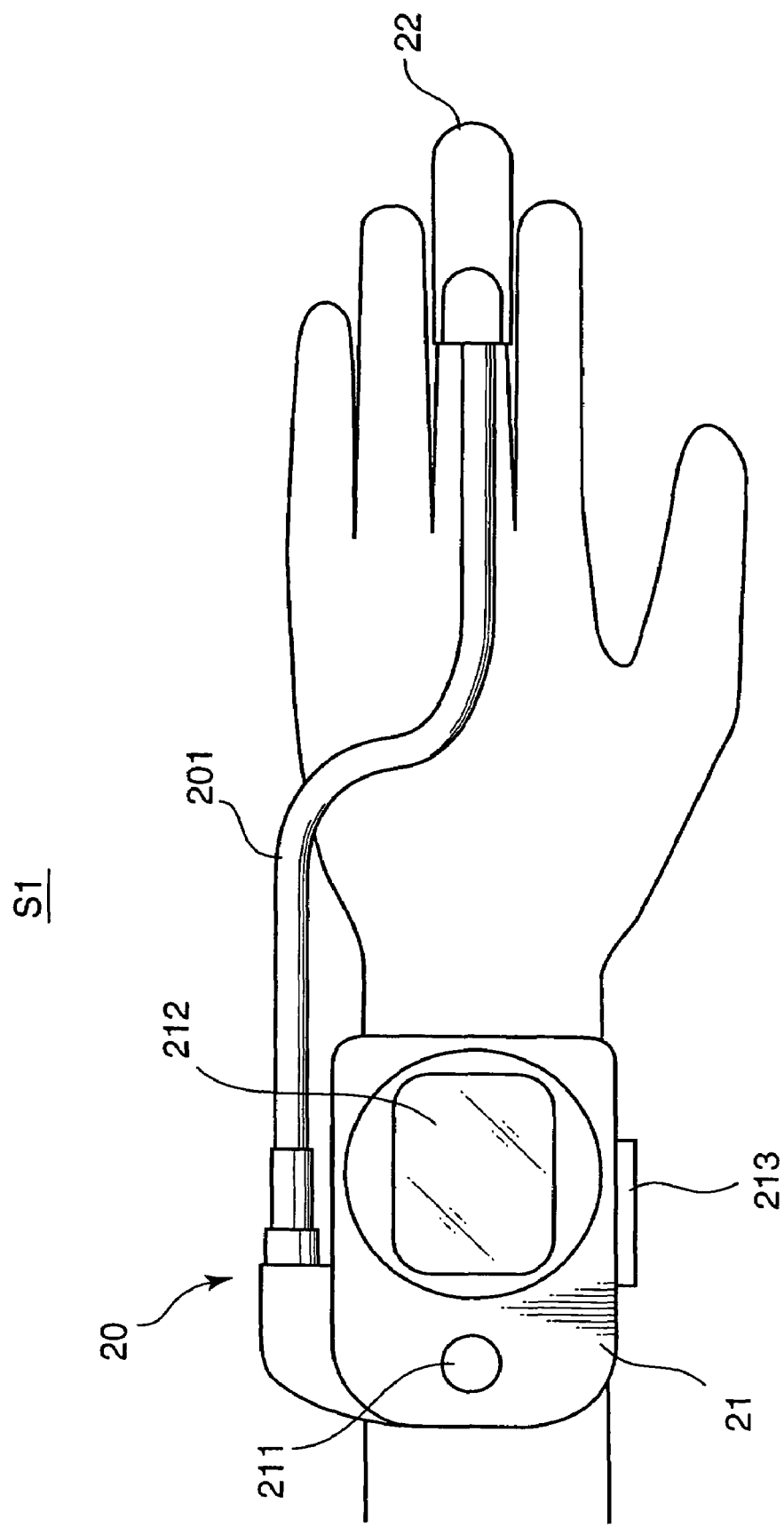
FIG. 2 is a diagram showing an external appearance of a pulse wave data analyzing system, as an example of a hardware construction of the pulse wave data analyzing system shown in FIG. 1.

The pulse wave data analyzing system "S0" having the above arrangement can be realized as various hardware constructions. FIG. 2 is a diagram showing an external appearance of a pulse wave data analyzing system "S1", wherein the pulse wave detector 11, the data analyzer 12, the display section 13, and the storage section 14 are mounted on a pulse wave measuring device 20 as a single device which is removably attachable to a subject. The pulse wave measuring device 20 i.e. the pulse wave data analyzing system "S1" includes a device main body 21 which is removably attachable to a site near a wrist of the subject, and a probe 22 which is removably attachable to a fingertip of the subject. The device main body 21 and the probe 22 are electrically connected by a signal cable 201.

The device main body 21 is internally provided with an electrical circuit serving as functional parts corresponding to a part of the pulse wave detector 11, the data analyzer 12, and the storage section 14, in addition to a power source switch 211, a display device 212 provided with an LCD, which corresponds to the display section 13, a belt locking portion 213, and the like. The probe 22 is provided with a light emitter and a light detector constituting a part of the pulse wave detector 11. With the pulse wave data analyzing system "S1", a system is realized as a single device where all the necessary functions are loaded and which is wearable to the subject, thereby providing a compact system with enhanced portability.

Figure 3:
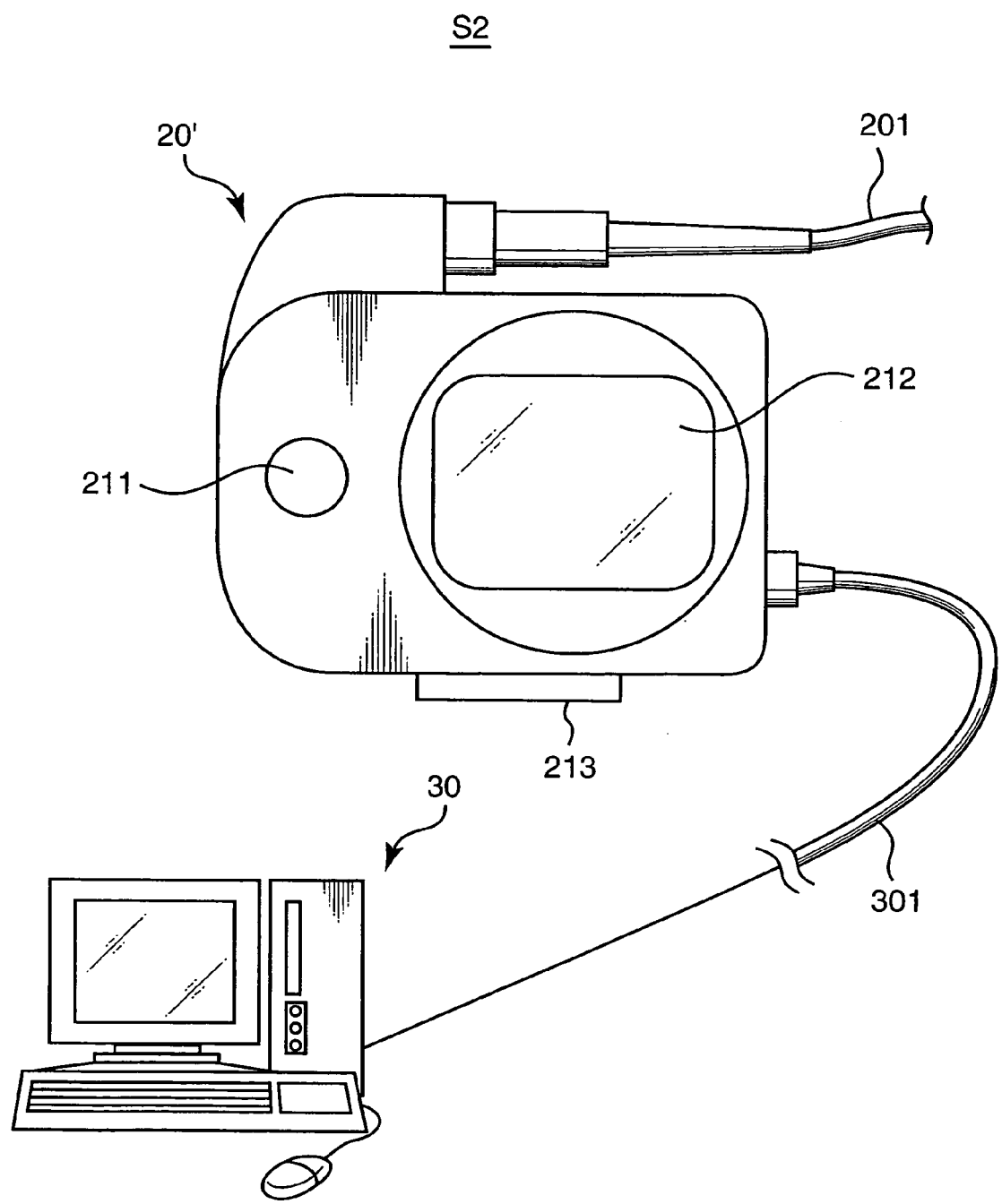
FIG. 3 is a diagram showing an external appearance of a pulse wave data analyzing system, as another example of a hardware construction of the pulse wave data analyzing system shown in FIG. 1.

FIG. 3 is a diagram showing another example of a hardware construction of the inventive system, showing an external appearance of a pulse wave data analyzing system "S2", wherein a pulse wave measuring device 20', as a first device, which is removably attachable to the subject, and a personal computer 30 as a second device are connected to each other by a communication cable such as a USB cable. In the pulse wave data analyzing system "S2", the function of the pulse wave detector 11 is provided in the pulse wave measuring device 20', and the functions of the data analyzer 12 and the display section 13 are provided in the personal computer 30. Alternatively, the pulse wave measuring device 20' may be provided with the functions of the data analyzer 12 and the display section 13. With the pulse wave data analyzing system "S2", the pulse wave measuring device 20' to be removably attached to the subject can be configured into a simplified construction, thereby providing enhanced wearability, while allowing the personal computer 30 to execute sophisticated data analysis.

Figure 4:
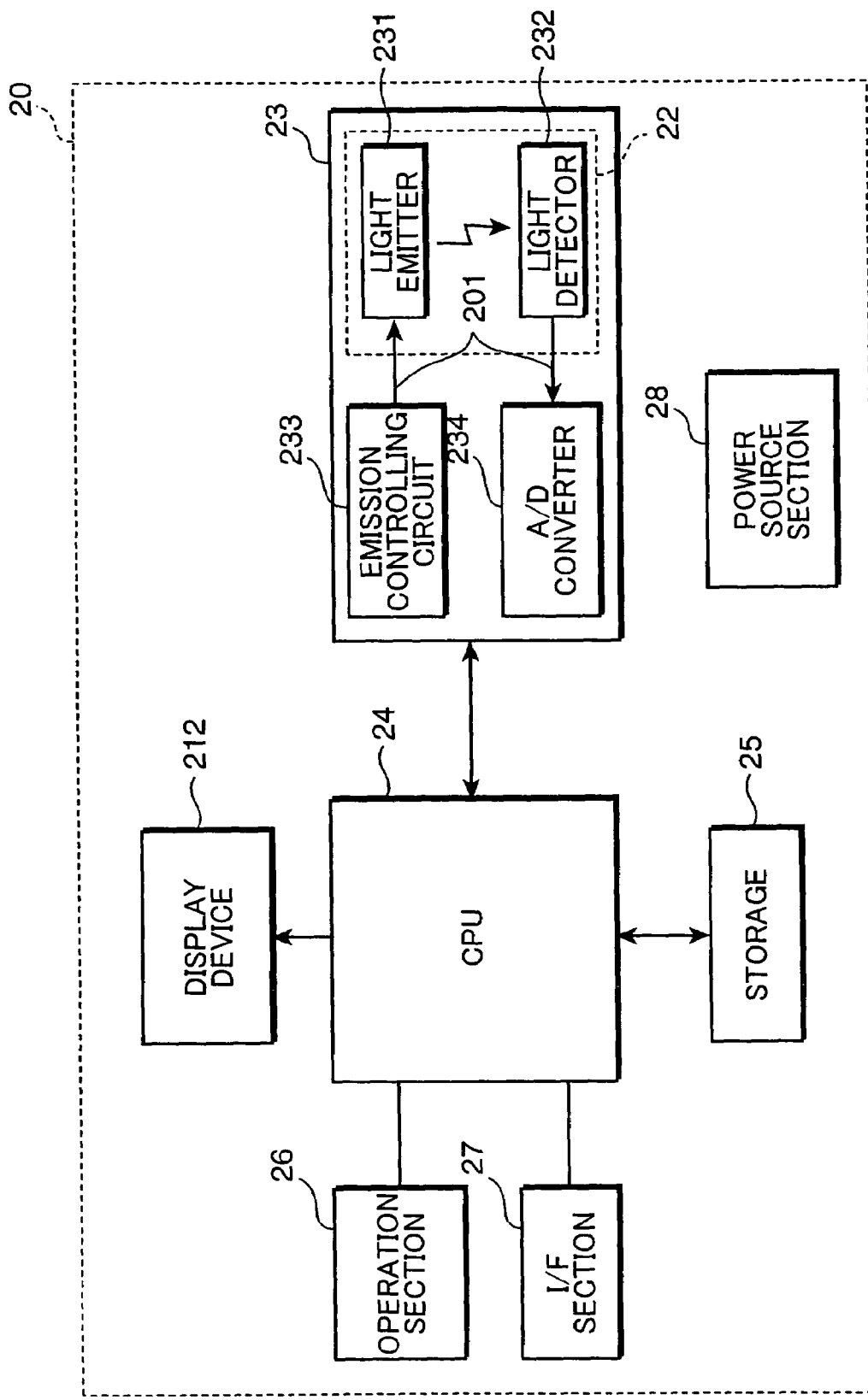
FIG. 4 is a block diagram showing an electrical configuration of a pulse wave measuring device shown in FIG. 2.

FIG. 4 is a block diagram showing an electrical configuration of the pulse wave measuring device 20 shown in FIG. 2. The pulse wave measuring device 20 includes, as electrical components, a sensing section 23 as a pulse wave detector, a CPU (Central Processing Unit) 24 as a data analyzer, a storage 25 as a storage section, an operation section 26, an I/F section 27, a power source section 28, and the aforementioned display device 212 as a display section.

The sensing section 23 is controlled by the CPU 24 i.e. a measurement controller 41 to be described later. The sensing section 23 measures pulse wave information concerning the subject at a predetermined sampling frequency e.g. 30 ms, and includes a light emitter 231, a light detector 232, an emission controlling circuit 233, and an A/D converter 234. The light emitter 231 and the light detector 232 are mounted on the probe 22. The emission controlling circuit 233 and the A/D converter 234 are mounted on the device main body 21. The emission controlling circuit 233 and the light emitter 231, and the light detector 232 and the A/D converter 234 are electrically connected with each other by signal cables 201, respectively. As described above, the light emitter 231 and the light detector 232 constitute a reflective or transmissive sensor utilizing a light absorption characteristic of hemoglobin in blood, and are mounted on the probe 22 at such positions as to define an optical path through a living tissue, in this embodiment, a fingertip of the subject.

The light emitter 231 is a light source provided with a light emitting device such as an LED of generating light of a predetermined wavelength $\lambda$. An emission operation of the light emitter 231 is controlled by the emission controlling circuit 233. The emission controlling circuit 233 generates a drive signal of causing the light emitter 231 to emit light at a predetermined sampling frequency, based on a measurement control signal issued from the CPU 24. The light detector 232 has a sensitivity at least to the light of the wavelength $\lambda$ emitted from the light emitter 231, and is a photoelectric conversion light receiving device of generating an electric current commensurate with the intensity of received light. An example of the light receiving device is a silicon photo diode. The A/D converter 234 converts an analog current which has been outputted from the light detector 232 commensurate with the received light intensity into a digital signal.

The amount of light received by the light detector 232, namely, the reflected light amount or the transmitted light amount, is varied depending on a cycle of a pulsation, because the amount of hemoglobin is varied by the pulsation of blood flow accompanied by a heartbeat in a pulse-like manner, and the light absorption amount is varied accordingly. Therefore, the digital signal, which is outputted from the A/D converter 234 at the sampling frequency in accordance with the received light amount, is recognized as information that reflects the pulsation condition in the respective sampling frequencies. The detected pulse wave information is stored in the storage 25 via the CPU 24 in association with time information.

The CPU 24 controls overall operations of the pulse wave measuring device 20 in accordance with a certain control program. The CPU 24 controls a pulse wave data acquiring operation to be executed the sensing section 23, a noise removal operation of removing notch noises included in the acquired raw pulse wave data, and an operation of obtaining peak-to-peak intervals or bottom-to-bottom intervals which appear on the pulse waveform, based on the pulse wave data obtained after the noise removal. A functional arrangement of the CPU 24 will be described later in detail referring to FIG. 5.

The storage 25 temporarily stores therein pulse wave data detected by the sensing section 23 i.e. data obtained by correlating the digital data outputted from the A/D converter 234 to the time information, data analysis results by the CPU 24 such as peak-to-peak intervals, bottom-to-bottom intervals, peak-to-bottom intervals of a pulse waveform which are calculated by an interval calculator 45 to be described later.

The operation section 26 includes various switches i.e. input buttons, and allows a user to input certain designation so as to operate the respective parts of the pulse wave measuring device 20. The operation section 26 is provided with, as the various switches, the power source switch 211 (see FIG. 2) for switching over the power of the power source section 28 between on-state and off-state, and a measurement switch for switching over the sensing section 23 between on-state and off-state to start or terminate a pulse wave data detection and a data analysis based on the detection information. Various arrangements are applicable as the switches such as a push button which is mechanically depressed, and an input button which is displayed on a touch panel of a liquid crystal display or a like device.

The I/F section 27 performs data communication with the personal computer 30 or a like device, as shown in FIG. 3, for instance, and is a data communication device in conformity to standards of wired communications e.g. RS-232C, USB, IrDA (Infrared Data Association), or wireless communications. An example of the wired communications is a network such as LAN.

The power source section 28 supplies a power to the respective parts of the pulse wave measuring device 20. Examples of the power source section 28 are a dry battery, a button battery, and an AC power section. The display section 212 displays the data analysis result concerning the pulse wave data by the CPU 24 in terms of textual information, image information, or the like.

Figure 5:
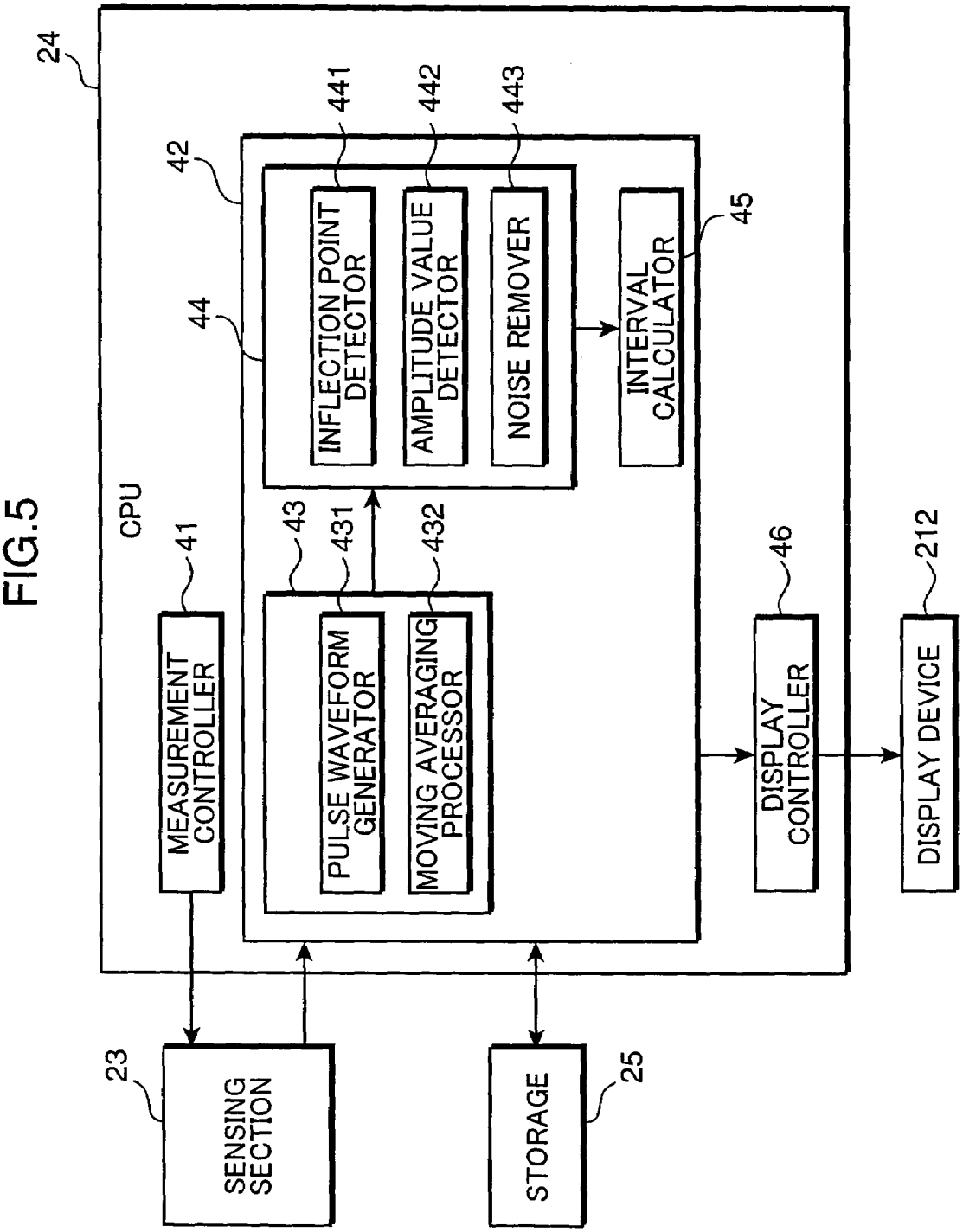
FIG. 5 is a block diagram showing functional parts of a CPU.

Next, the functional arrangement of the CPU 24 is described. FIG. 5 is a block diagram showing the functional parts of the CPU 24. The CPU 24 functionally includes the measurement controller 41, a data analyzer 42, and a display controller 46.

The measurement controller 41 controls the pulse wave data acquiring operation to be executed by the sensing section 23. The measurement controller 41 generates an emission control signal at a predetermined sampling frequency, using a certain timer function, and sends the emission control signal to the emission controlling circuit 233 (see FIG. 4). The measurement controller 41 receives the digital signal outputted from the A/D converter 234 in synchronism with the transmission of the emission control signal, and reads the pulse wave information into the storage 25 in association with the time information.

The display controller 46 performs a data process so that the data analysis result concerning the pulse wave data to be executed by the CPU 24 is displayed on the display section 212 as a proper indication.

The data analyzer 42 performs various data analyzing processes with respect to the pulse wave data that has been acquired by the sensing section 23 and temporarily stored in the storage 25, or directly with respect to the raw pulse wave data detected by the sensing section 23. The data analyzer 42 includes a preprocessor 43, a noise removal processor 44, and the interval calculator 45.

The preprocessor 43 is a functioning part for performing a predetermined preprocess with respect to the raw pulse wave data acquired by the sensing section 23 prior to a notch noise removal process to be executed by the noise removal processor 44. The preprocessor 43 includes a pulse waveform generator 431 and a moving averaging processor 432. The pulse waveform generator 431 performs a data aligning process of developing the pulse wave data that has been acquired at the predetermined sampling frequency, and stored in the storage 25 in association with the time information along a time axis to generate a pulse waveform.

The moving averaging processor 432 performs a moving averaging process with respect to the pulse waveform generated by the pulse waveform generator 431, and performs a smoothing process. For instance, the moving averaging processor 432 obtains an average with respect to five pulse wave data plotted on a time axis of the pulse waveform, i.e. with respect to central data, and two consecutive data each preceding and succeeding to the central data, and executes the averaging with respect to the pulse waveform sequentially along the time axis. The moving averaging process has the following advantages.

Figure 6:
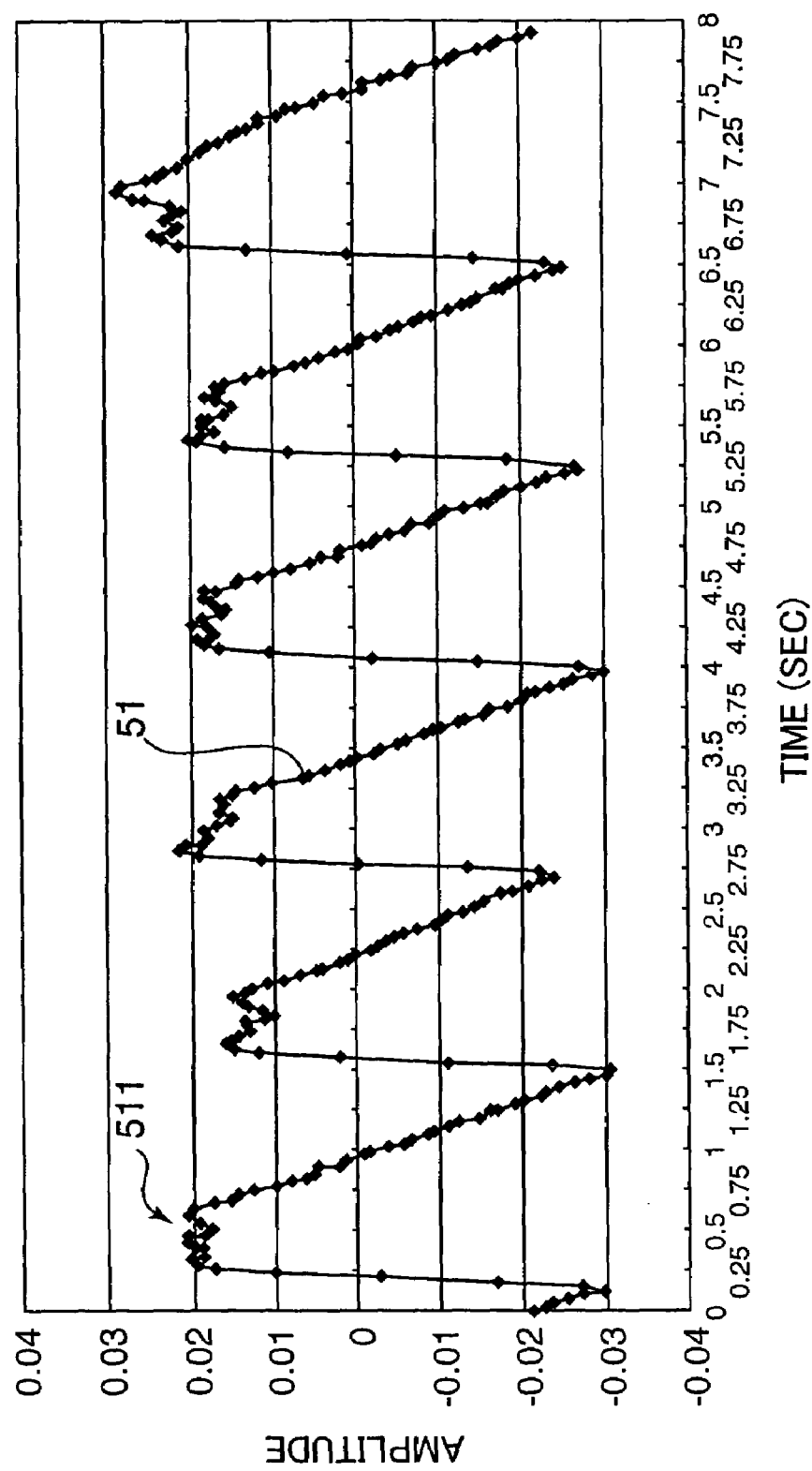
FIG. 6 is a graph showing a pulse waveform generated by a pulse waveform generator.

FIG. 6 is a graph showing a pulse waveform 51 generated by the pulse waveform generator 431 at a sampling frequency of 26.7 ms. The pulse waveform 51 is a raw pulse waveform which is obtained by plotting raw pulse wave data. As shown in FIG. 6, a superimposed noise, as indicated by the numeral 511, frequently appears on the raw pulse waveform 51 within a small measurement duration. The noise in the pulse wave data is also recognized as a bottom value and a peak value, which obstructs a high-speed processing in the case where the noise removal processor 44 performs a notch noise removal process, using the raw pulse waveform 51.

Figure 7:
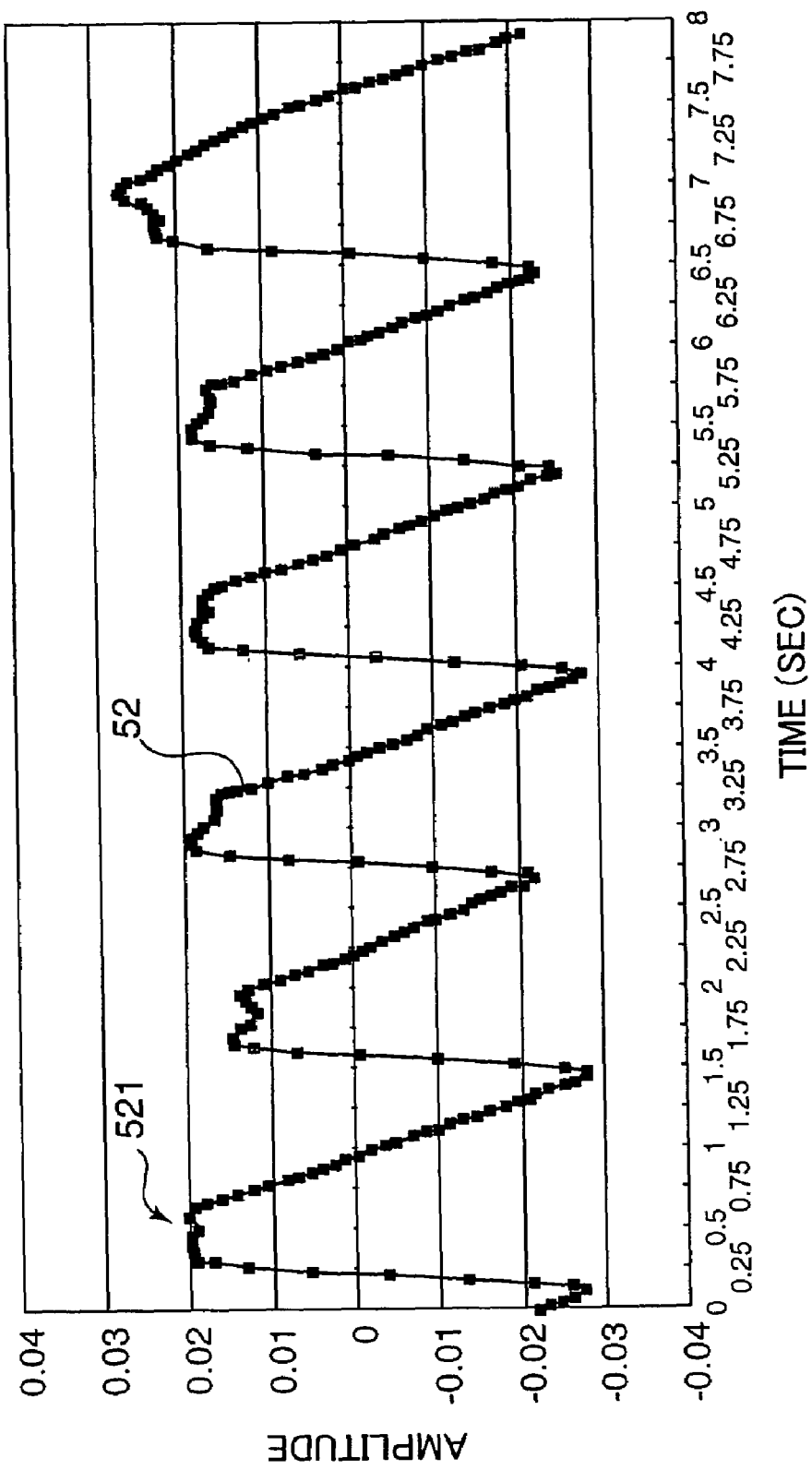
FIG. 7 is a graph showing a pulse waveform after a moving averaging process.

In view of the above, the moving averaging processor 432 performs the aforementioned moving averaging process with respect to the raw pulse waveform 51 to smooth the raw pulse waveform 51. FIG. 7 is a graph showing a pulse waveform 52 obtained by executing the moving averaging process. A portion indicated by the numeral 521 in the pulse waveform 52 corresponds to the portion indicated by 511 in the raw pulse waveform 511 shown in FIG. 6. It is clear from FIG. 7 that the portion 521 is smoothed by the moving averaging process. This enables to simplify a process of extracting bottom values and peak values by the noise removal processor 44.

The noise removal processor 44 performs a process of removing notch noises out of the pulse waveform 52 after the moving averaging process in FIG. 7, and includes an inflection point detector 441, an amplitude value detector 442, and a noise remover 443. The inflection point detector 441 performs a process of sequentially detecting bottom values and peak values along the time axis out of the pulse waveform 52 after the moving averaging process in FIG. 7, which serves as pulse wave data. Specifically, the inflection point detector 441 sequentially compares plot data constituting the pulse waveform 52 along the time axis, detects a turning point at which the pulse waveform 52 is changed from a falling to a rising, as a bottom value, and detects a turning point at which the pulse waveform 52 is changed from a rising to a falling, as a peak value. FIG. 8 shows a manner as to how the bottom values and the peak values are detected with respect to the pulse waveform 52. Referring to FIG. 8, the reference numerals "B1" through "B5" denote bottom values, and the reference numerals "P1" through "P5" denote peak values, respectively.

The amplitude value detector 442 makes pairs each consisting of a bottom value and a peak value adjacent to each other along the time axis, using the bottom values "B1" through "B5", and the peak values "P1" through "P5" detected by the inflection point detector 441, and obtains a bottom-to-peak amplitude value, which is a difference between the bottom value and the peak value in each of the pairs, with respect to each of the pairs along the time axis. The process is described in detail, referring to FIG. 8. First, the bottom value "B1" and the peak value "P1" (see an enlarged illustration of a portion 522 in an upper left section of FIG. 8), which appear for the first time in the pulse waveform 52 on the time axis make a pair, and a first bottom-to-peak amplitude value "SW1" is calculated by obtaining a difference between the bottom value "B1" and the peak value "P1". Similarly to the above, the bottom value and the peak value adjacent to each other make a pair in such a manner that the bottom value "B2" and the peak value "P2", the bottom value "B3" and the peak value "P3", the bottom value "B4" and the peak value "P4", and the bottom value "B5" and the peak value "P5" make pairs, respectively. Then, a second bottom-to-peak amplitude value "SW2", a third bottom-to-peak amplitude value "SW3", a fourth bottom-to-peak amplitude value "SW4", and a fifth bottom-to-peak amplitude value "SW5" are obtained by obtaining a difference between the bottom value and the peak value with respect to each of the pairs. The same process is executed with respect to bottom values and peak values which appear in the rest of the pulse waveform 52.

The noise remover 443 sequentially compares the bottom-to-peak amplitude values adjacent to each other on the time axis with respect to the bottom-to-peak amplitude values "SW1" through "SW5" obtained by the amplitude value detector 442, and removes the bottom value and the peak value concerning the smaller bottom-to-peak amplitude value of the two adjacent bottom-to-peak amplitude values for a data process to be executed thereafter, if a ratio of the two adjacent bottom-to-peak amplitude values is judged to be larger than a predetermined value. Among the first through fifth bottom-to-peak amplitude values "SW1" through "SW5" shown in FIG. 8, the first bottom-to-peak amplitude value "SW1", the third first bottom-to-peak amplitude value "SW3", and the fifth bottom-to-peak amplitude value "SW5" are relatively large amplitude values. Accordingly, the peak values "P1", "P3", and "P5", or the bottom values "B1", "B3", and "B5" concerning the first, the third, and the fifth bottom-to-peak amplitude values "SW1", "SW3", and "SW5" are assessed to be significant data in detecting pulse wave peak-to-peak intervals. However, the second and the fourth bottom-to-peak amplitude values "SW2" and "SW4" are relatively small amplitude values, which are presumably recognized as notch noises. Accordingly, the noise remover 443 erases the bottom values "B2" and "B4", and the peak values "P2" and "P4" concerning the second and the fourth bottom-to-peak amplitude values "SW2" and "SW4" out of the pulse waveform 52.

An example of the process to be executed by the noise remover 443 is described. First, the noise remover 443 compares the first bottom-to-peak amplitude value "SW1" which appears for the first time on the time axis, with the second bottom-to-peak amplitude value "SW2" which appears following the first bottom-to-peak amplitude value "SW1", and determines the second bottom-to-peak amplitude value "SW2" as a notch noise if a ratio of the second bottom-to-peak amplitude value "SW2" to the first bottom-to-peak amplitude value "SW1" is equal to or smaller than a predetermined relative value "a". Then, the noise remover 443 compares the second bottom-to-peak amplitude value "SW2" with the third bottom-to-peak amplitude value "SW3" which appears following the second bottom-to-peak amplitude value "SW2", and judges whether the third bottom-to-peak amplitude value "SW3" is to be recognized as a notch noise based on a judgment as to whether a ratio of the third bottom-to-peak amplitude value "SW3" to the second bottom-to-peak amplitude value "SW2" is equal to or smaller than the predetermined relative value "a". The noise remover 443 performs the same judgment process with respect to the rest of the pulse waveform 52 by sequentially comparing bottom-to-peak amplitude values adjacent to each other on the time axis.

In other words, in the aforementioned example, the noise remover 443 sequentially performs a computation expressed by the following formula (1) with respect to the bottom-to-peak amplitude values adjacent to each other on the time axis, and judges that the bottom-to-peak amplitude value ($SW_{i+1}$) which appears following the bottom-to-peak amplitude value ($SW_i$) on the time axis is a notch noise under a condition that the formula (1) is satisfied.

$$SW_i * a > SW_{i+1} \quad (1)$$

where "i" is an integer from 1 to n;
"n" is the total number of bottom-to-peak amplitude values detected with respect to the pulse waveform 52; and
"a" is an arbitrarily set relative value of 1 or less.

The relative value "a" used in the formula (1) is arbitrarily set depending on a feature of pulsation of a subject or a predicted symptom. Generally, a notch is exceedingly small as compared with a pulse wave component, and a relative ratio of adjacent bottom-to-peak amplitude values corresponding to the notch is about 30% as large or less to a relative ratio of adjacent bottom-to-peak amplitude values corresponding to the pulse wave component. In view of this, a relative value "a"=0.3 can be defined as a default, for instance. Applying the aforementioned judgment process to the first through fifth bottom-to-peak amplitude values "SW1" through "SW5" shown in FIG. 8, and calculating relative ratios of SW2 to SW1, SW3 to SW2, SW4 to SW3, and SW5 to SW4 obviously satisfies the formula (1) in comparison and judgment concerning the ratios of SW2 to SW1, and SW4 to SW3. In this arrangement, the noise remover 443 judges the second and the fourth bottom-to-peak amplitude values "SW2" and "SW4" as notch noises, and removes the bottom values "B2" and "B4", and the peak values "P2" and "P4" concerning the second and the fourth bottom-to-peak amplitude values "SW2" and "SW4" out of the pulse waveform 52, so that these values may not be used in a data process to be executed thereafter.

Figure 9:
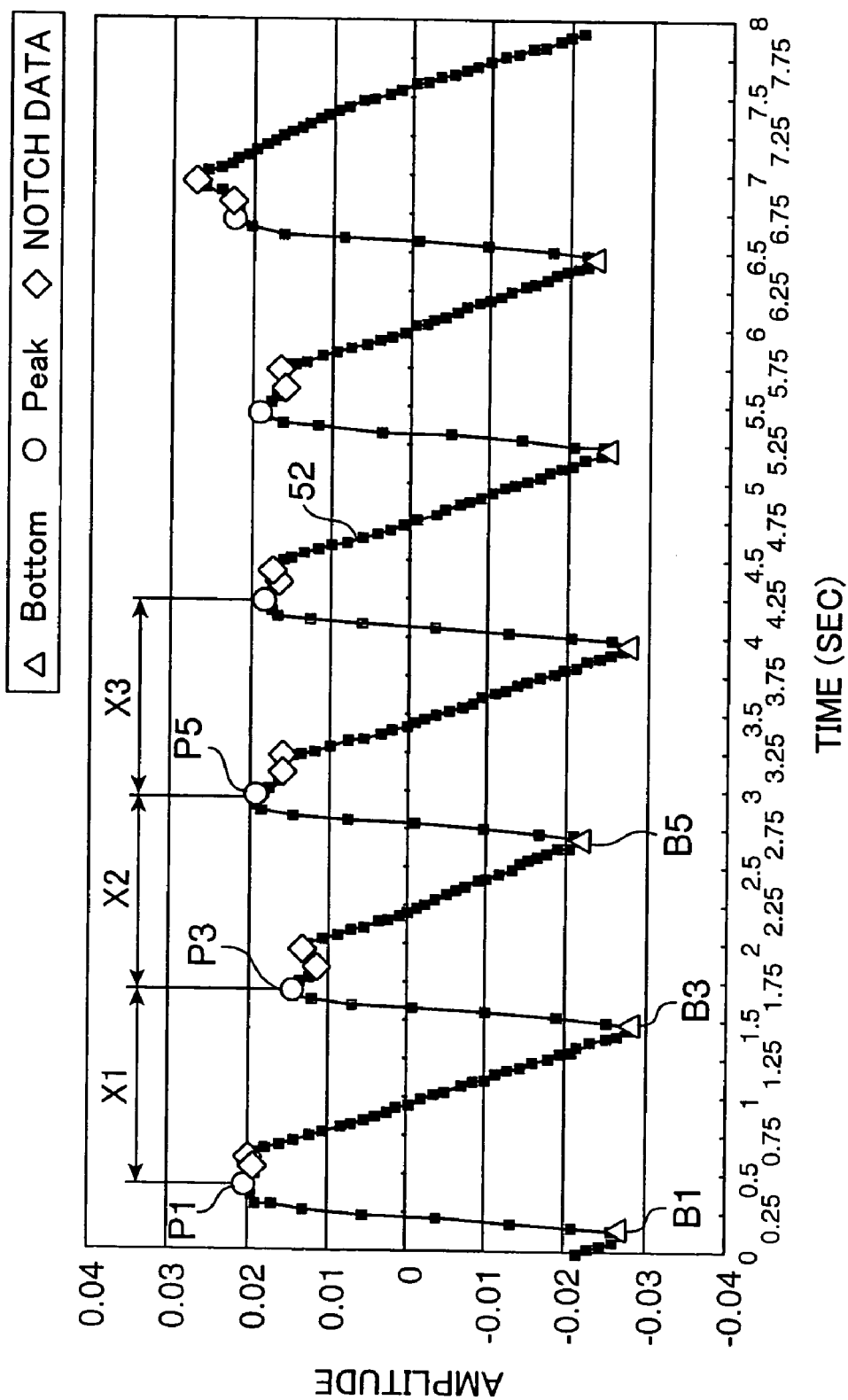
FIG. 9 is a graph showing a manner as to how notch noises are removed.

As a result of the above removal process, as shown in FIG. 9, the peak values "P1", "P3", and "P5", and the bottom values "B1", "B3", and "B5" remain as peak values and bottom values in a data process. In other words, the peak values "P2" and "P4", and the bottom values "B2" and "B4" are erased as notch noises, and the peak values or bottom values that have a true correlation to the heartbeat are left. In this way, accurate pulse wave peak-to-peak intervals can be calculated by obtaining a time interval "X1" between the peak value "P1" and the peak value "P3", a time interval "X2" between the peak value "P3" and the peak value "P5", and so on. Alternatively, a time interval between the bottom value "B1" and the bottom value "B3", a time interval between the bottom value "B3" and the bottom value "B5", and so on, may be obtained.

The noise removal processor 44 repeats a through-process i.e. the noise removal process from a start point to an end point of the pulse waveform along the time axis until bottom-to-peak amplitude values having possibility of notch noise are completely erased. It should be noted that the configuration of the pulse waveform i.e. an appearance manner of notch noises differs among the subjects, and there is a case that a one-time through-process along the time axis cannot completely remove the notch noises. This point is described by an example of a pulse waveform 53 shown in FIG. 10.

Figure 10:
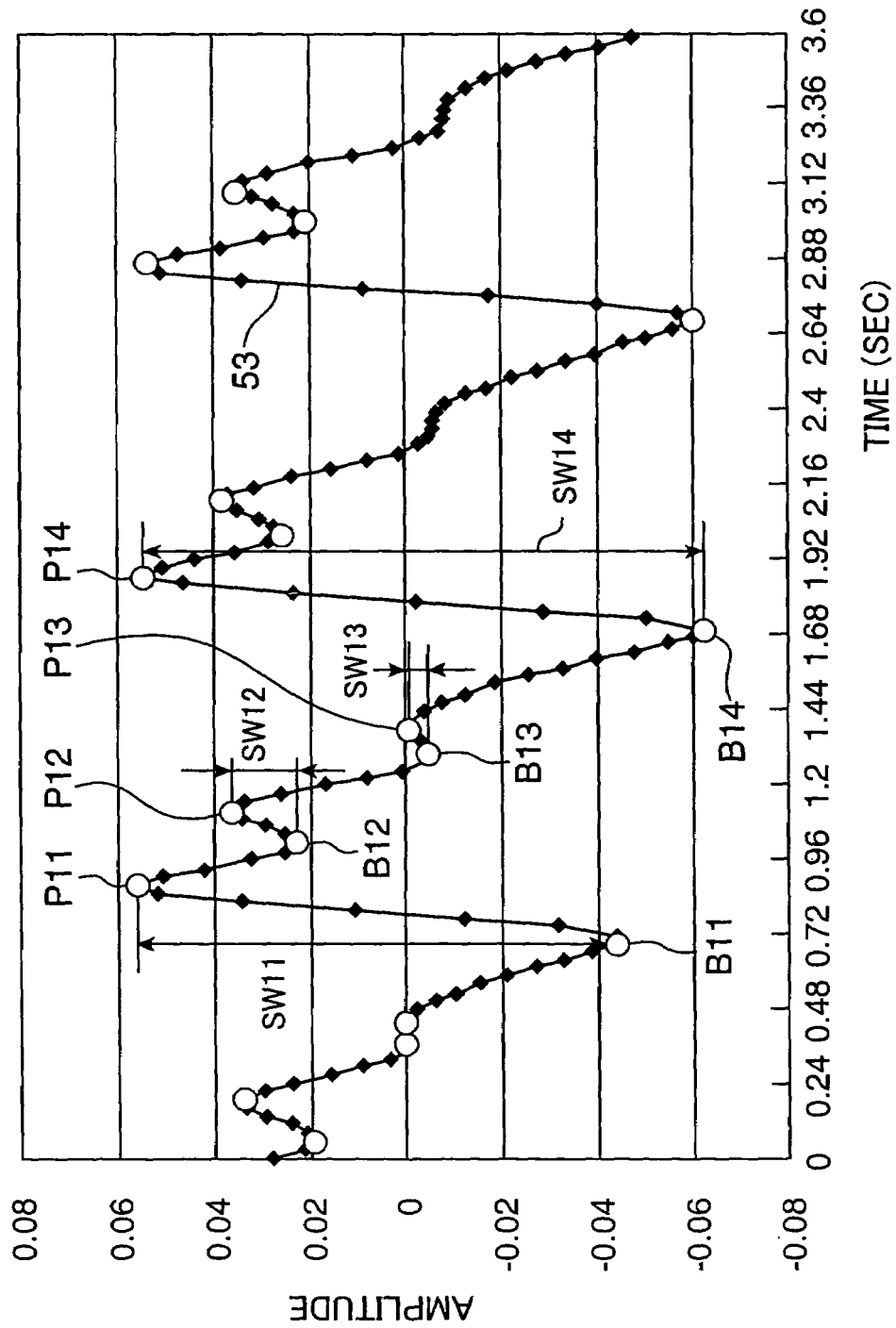
FIG. 10 is a graph showing another example of a pulse waveform.

In the pulse waveform 53 shown in FIG. 10, the inflection point detector 441 detects bottom values "B11" through "B14", and peak values "P11" through "P14". The amplitude value detector 442 detects first through fourth bottom-to-peak amplitude values "SW11" through "SW14" based on the detected bottom values and the peak values. In this example, the second and the third bottom-to-peak amplitude values "SW12" and "SW13", which are small amplitude values and are presumably recognized as notches, are detected between the first and the fourth bottom-to-peak amplitude values "SW11" and "SW14", which are large amplitude values. In this example, if the noise remover 443 sequentially performs computation of obtaining ratios of SW12 to SW11, SW13 to SW12, and SW14 to SW13 using the formula (1), the second bottom-to-peak amplitude value "SW12" is judged to be a notch noise in obtaining the ratio of SW12 to SW11, because the second bottom-to-peak amplitude value "SW12" is significantly small relative to the first bottom-to-peak amplitude value "SW11". In obtaining the ratio of SW13 to SW12, however, the third bottom-to-peak amplitude value "SW13" cannot be judged to be a notch noise because both the second and the third bottom-to-peak amplitude values "SW12" and "SW13" are small. Accordingly, in this example, the bottom value "B13" and the peak value "P13" concerning the third bottom-to-peak amplitude value "SW13" are left, whereas the bottom value "B12" and the peak value "P12" concerning the second bottom-to-peak amplitude value "SW12" are erased.

As mentioned above, there is likelihood that a notch noise may not be removed by a one-time through-process along the time axis. In view of this, the noise removal processor 44 erases the second bottom-to-peak amplitude value "SW12" for a data process, and performs a second-time through-process along the time axis. Since the second bottom-to-peak amplitude value "SW12" has already been erased in executing the second-time through-process, the noise removal processor 44 sequentially performs computation of obtaining ratios of SW11 to SW13, and SW13 to SW14. Since the third bottom-to-peak amplitude value "SW13" is significantly small relative to the first bottom-to-peak amplitude value "SW11" in comparison of SW11 and SW13, the third bottom-to-peak amplitude value "SW13" is judged to be a notch noise, and accordingly erased. In this way, the noise removal processor 44 stores the number of peak values in advance, for instance, judges whether the number of peak values is decreased before and after a through-process by counting the number of peak values each time the through-process is executed along the time axis, in other words, judges whether there exists a bottom-to-peak amplitude value which has been judged to be a notch noise and accordingly erased in the preceding through-process, and cyclically repeats the noise removal process until the number of peak values is identical to each other before and after the through-process. Performing the above operations by the noise removal processor 44 enables to completely remove the notch noises.

The interval calculator 45 calculates peak-to-peak intervals or bottom-to-bottom intervals, based on the pulse waveform after the noise removal process by the noise remover 443. For instance, the interval calculator 45 performs computation of obtaining a time interval "X1" between the peak value "P1" and the peak value "P3" based on the time information stored in association with the peak value "P1", and the time information stored in association with the peak value "P3" with respect to the pulse waveform 53 shown in FIG. 9, for instance. Likewise, the interval calculator 45 performs computation of obtaining the time interval "X2" between the peak value "P3" and the peak value "P5", and so on with respect to the rest of the pulse waveform 52 along the time axis.

Figure 11:
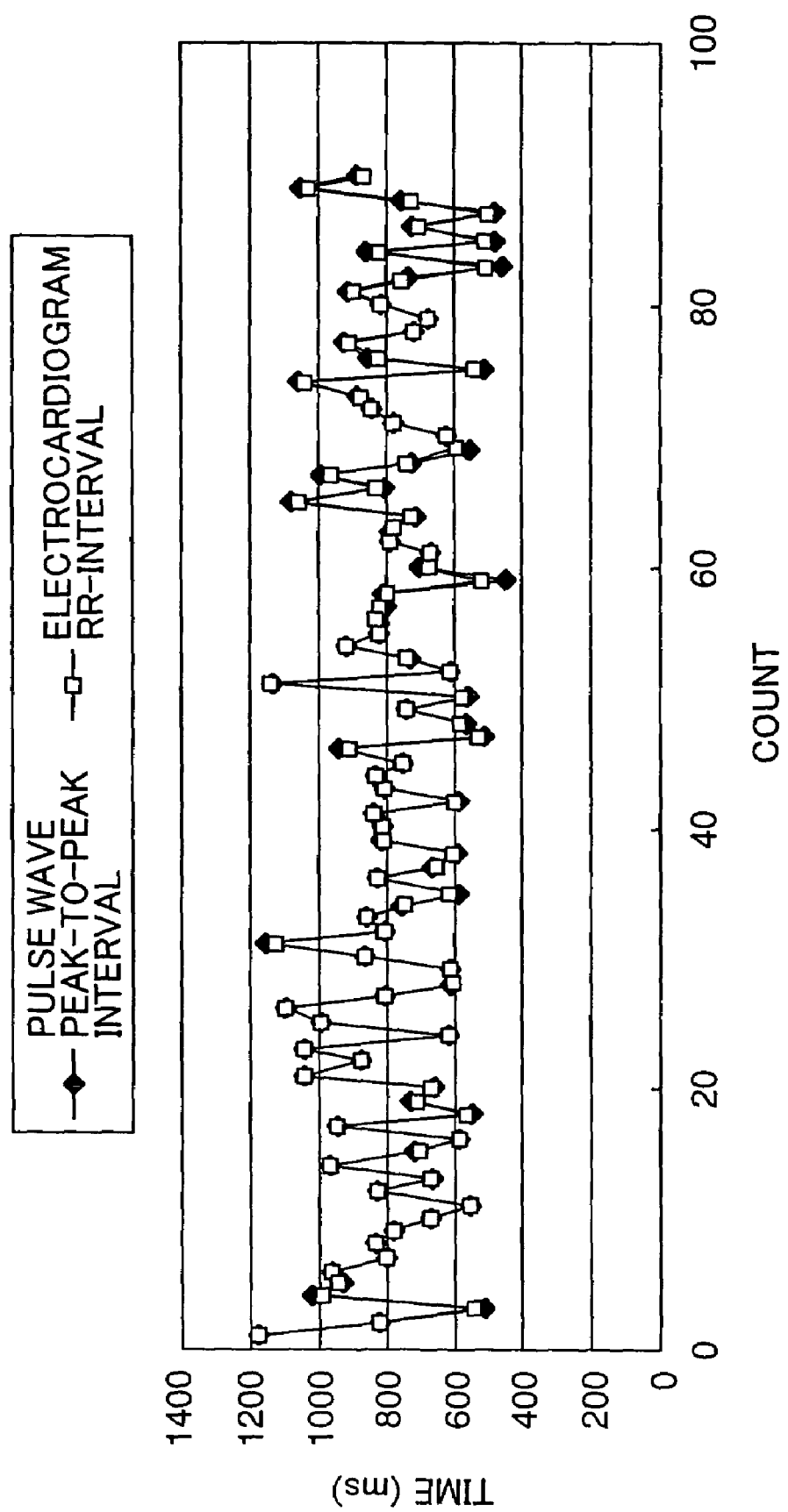
FIG. 11 is a graph showing electrocardiogram RR-intervals and pulse wave peak-to-peak intervals.

With the data analyzer 42 having the above configuration, notch noises are sequentially removed, as compared with an arrangement of obtaining peak-to-peak intervals or bottom-to-bottom intervals out of the raw pulse waveform 51 shown in FIG. 6. This enables to detect pulse wave peak-to-peak intervals having a high correlation to RR-intervals in an electrocardiogram. FIG. 11 is a graph expressing electrocardiogram RR-intervals and pulse wave peak-to-peak intervals along a common time axis by removably attaching an electrocardiograph and the pulse wave measuring device 20 of the embodiment to a subject, and by measuring an electrocardiogram and a pulse wave concurrently for a certain period. As shown in FIG. 11, the electrocardiogram RR-intervals and the pulse wave peak-to-peak intervals are substantially identical to each other, which clarifies that the data analyzer 42 is capable of obtaining information substantially equivalent to electrocardiogram RR-intervals.

The electrocardiogram RR-intervals i.e. the pulse wave PP-intervals in FIG. 11 show a measurement result in a subject in an event that an atrial fibrillation has occurred, and resultantly an arrhythmia has occurred. While the arrhythmia has occurred, the electrocardiogram RR-intervals show irregularities as shown in FIG. 11. If the interval calculator 45 calculates a time interval in a state that a peak portion corresponding to a notch noise is included in measuring the pulse wave peak-to-peak intervals having a high correlation to the electrocardiogram RR-intervals, it is difficult to judge whether the irregularities indicate fluctuations of pulse wave peak-to-peak intervals due to the arrhythmia, or fluctuations of pulse wave peak-to-peak intervals due to inclusion of a notch noise. As a result, reliability on measurement results may be lowered. In view of this, it is essentially important that the noise removal processor 44 should perform the notch noise removal process prior to calculation of the pulse wave peak-to-peak intervals by the interval calculator 45.

Figure 12:
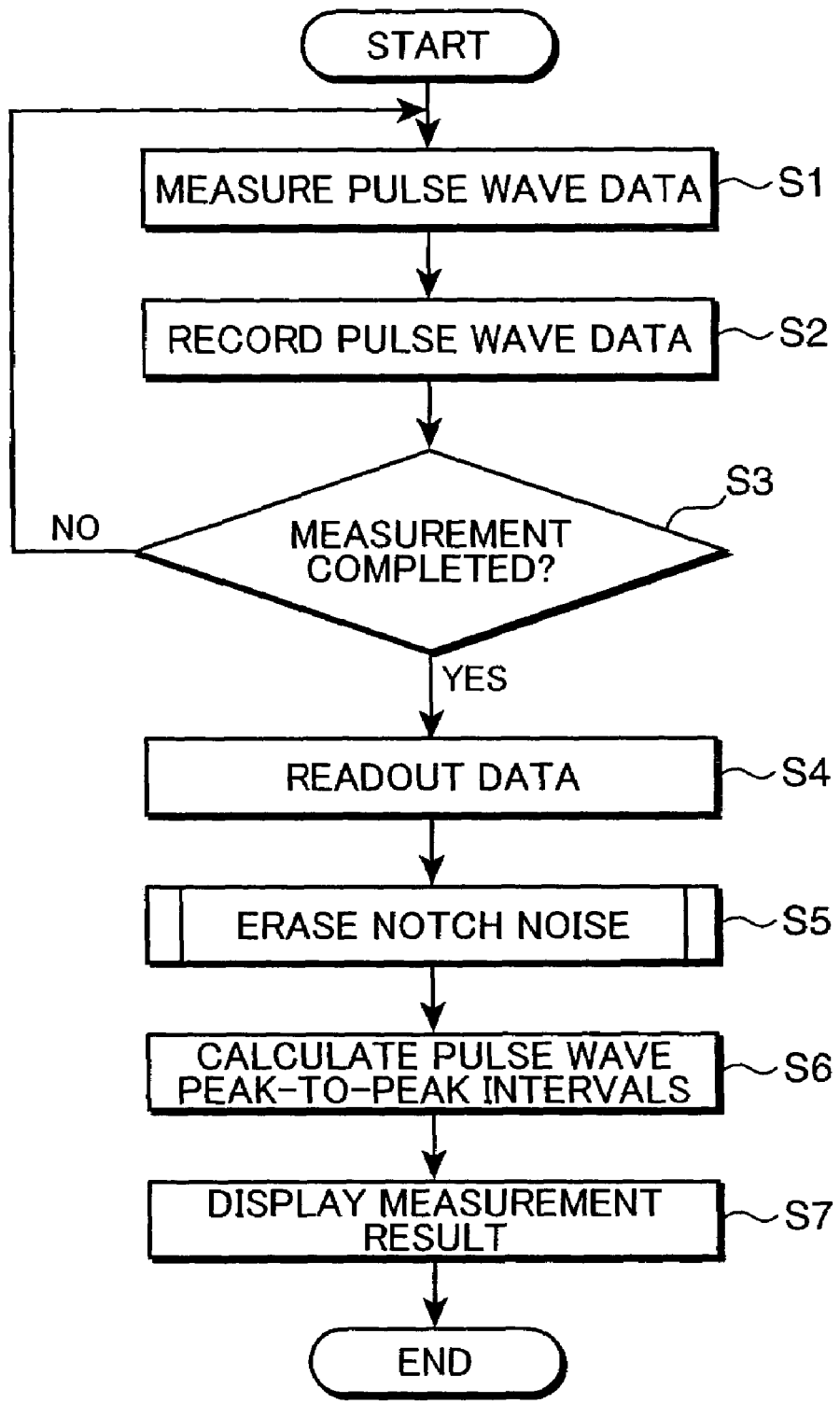
FIG. 12 is a flowchart showing an entire flow of calculating the pulse wave peak-to-peak intervals by the pulse wave measuring device.

An operation of the pulse wave measuring device 20 having the above configuration is described. FIG. 12 is a flowchart showing an overall flow on calculating pulse wave peak-to-peak intervals by the pulse wave measuring device 20. In this example, the flow is described for a case that pulse wave data measured within a predetermined period is temporarily stored in the storage 25, followed by reading out the pulse wave data therefrom by the data analyzer 42 to calculate pulse wave peak-to-peak intervals.

Referring to FIG. 12, upon completion of a pulse wave measurement preparatory operation by the pulse wave measuring device 20 by removably attaching the probe 22 onto a fingertip of a subject to be measured, the measurement controller 41 of the CPU 24 controls the sensing section 23 to acquire pulse wave data at a predetermined sampling frequency (Step S1). Then, the measurement controller 41 records digital pulse wave data outputted from the A/D converter 234 into the storage 25 in association with time information (Step S2). Subsequently, the measurement controller 41 judges whether a measurement operation for a predetermined period has been completed based on timer information or the like (Step S3). If the measurement controller 41 judges that the measurement operation has not been completed (NO in Step S3), the routines repeats the operations in Steps S1 and S2, and waits for a next sampling frequency.

If, on the other hand, the measurement controller 41 judges that the measurement operation has been completed (YES in Step S3), the data analyzer 42 reads out the pulse wave data recorded in the storage 25 (Step S4). Then, after the preprocessor 43 executes a predetermined preprocess such as a moving averaging process with respect to the pulse wave data, the noise removal processor 44 executes a noise removal process of removing notch noises (Step S5). Thereafter, the interval calculator 45 calculates pulse wave peak-to-peak intervals based on the pulse wave data after the noise removal process (Step S6). Then, the display controller 46 controls the display device 212 to display a measurement result in a proper indication format after a certain data process for the proper indication is implemented (Step S7). Thus, the process of calculating pulse wave peak-to-peak intervals by the pulse wave measuring device 20 is completed.

Figure 13:
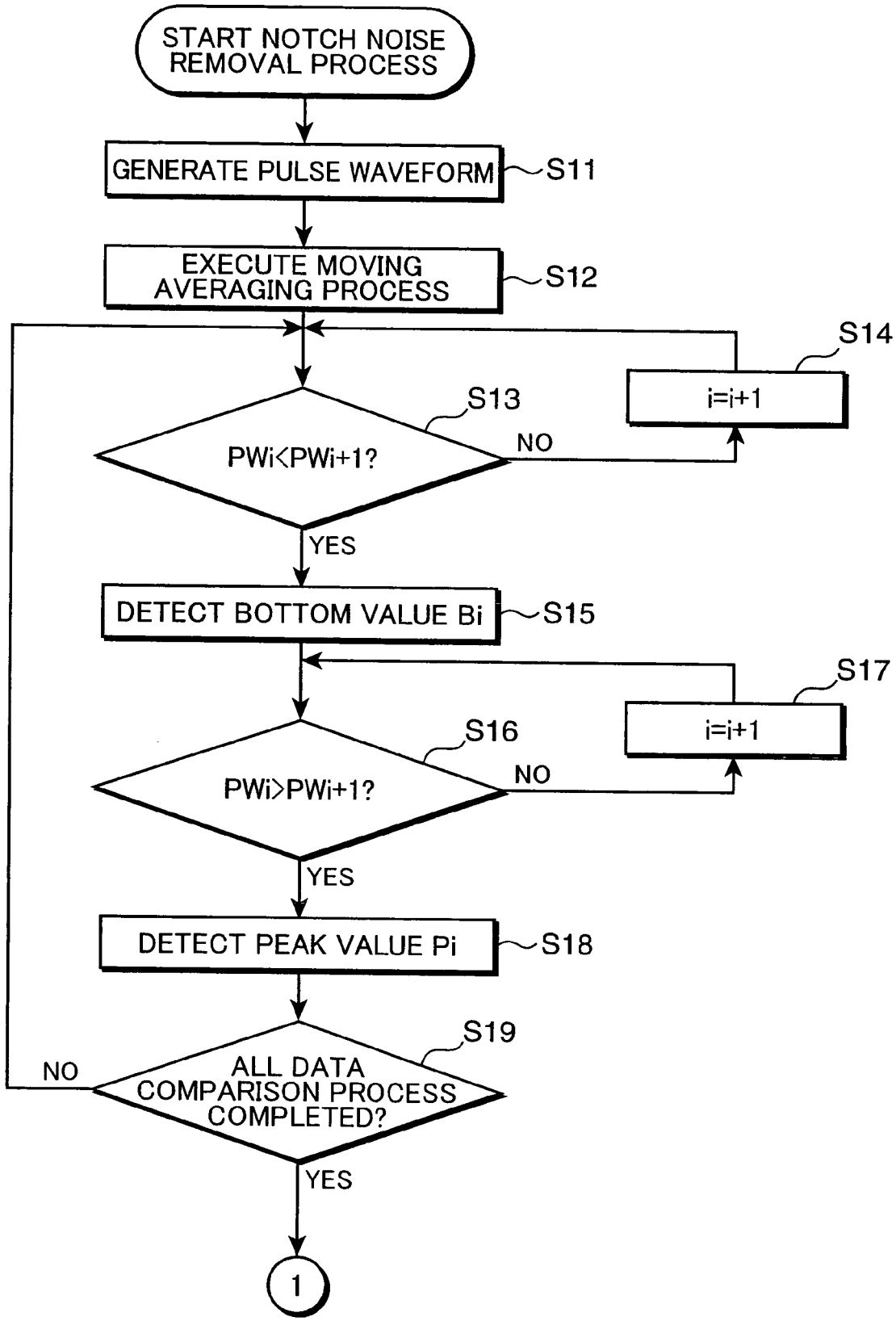
FIGS. 13 and 14 are flowcharts showing a detailed flow on a notch noise removal process.
Figure 14:
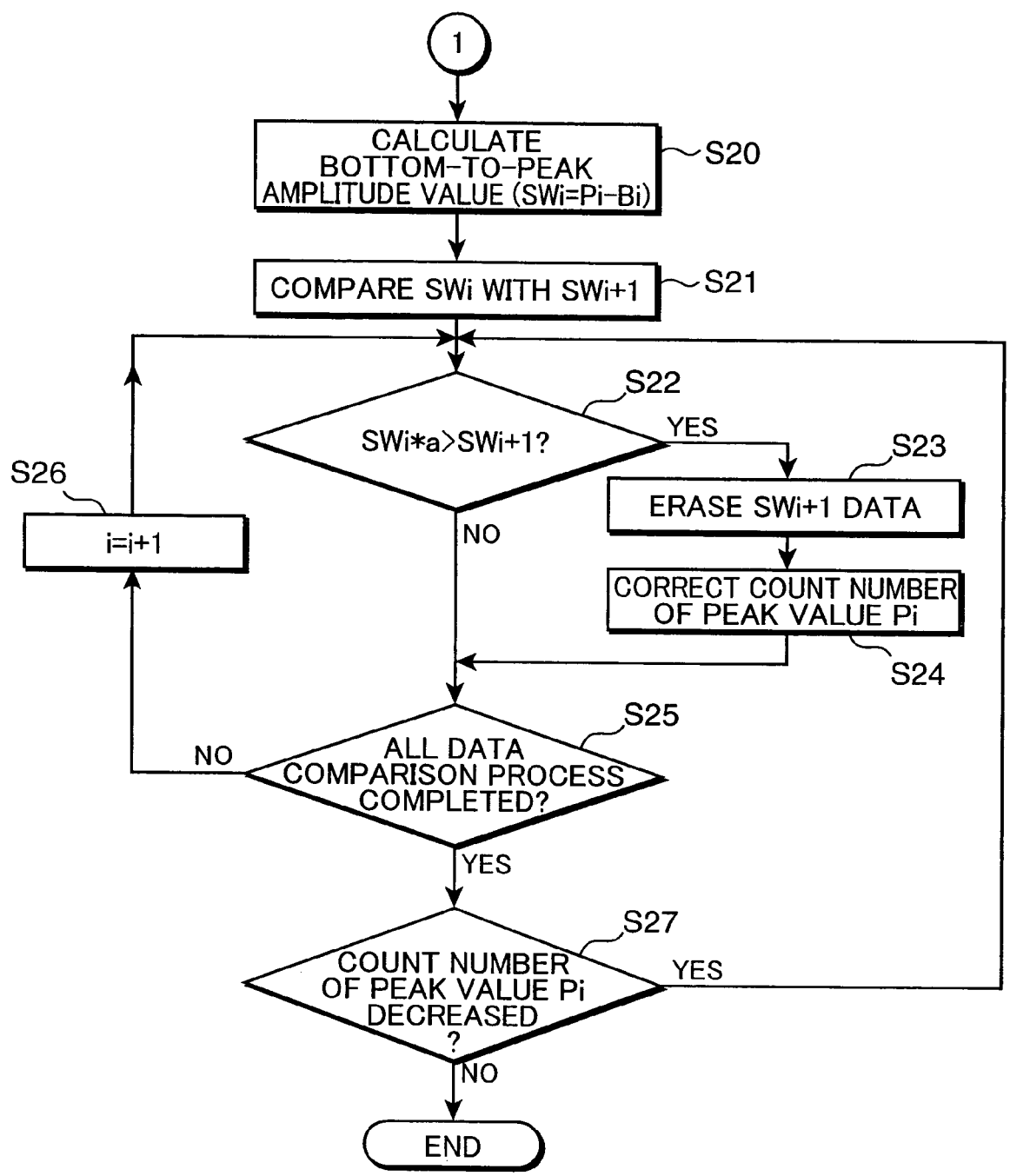

FIGS. 13 and 14 are flowcharts showing a detailed flow on the notch noise removal process in Step S5. When the pulse wave data is read out from the storage 25, the pulse waveform generator 431 performs a data aligning process of developing the pulse wave data along a time axis, and generates the pulse waveform as shown in FIG. 6 (Step S11). The moving averaging processor 432 performs a moving averaging process with respect to the pulse waveform so that the smoothed pulse waveform as shown in FIG. 7 is obtained (Step S12). The above is the preprocess operation.

Next, the inflection point detector 441 of the noise removal processor 44 sequentially detects bottom values and peak values along the time axis out of the pulse waveform after the moving averaging process. Specifically, the inflection point detector 441 compares a pulse wave value $PW_i$ constituting the pulse waveform, with a pulse wave value $PW_{i+1}$ adjacent to the pulse wave value $PW_i$ on the time axis to judge whether a relation: $PW_i < PW_{i+1}$ is satisfied (Step S13). If the relation: $PW_i < PW_{i+1}$ is not satisfied (NO in Step S13), the counter "i" is incremented by one (Step S14), and the operation in Step S13 is repeated with respect to a pair of the succeeding pulse wave values on the time axis. If, on the other hand, the relation: $PW_i < PW_{i+1}$ is satisfied (YES in Step S13), the judgment result means that the pulse waveform is changed from a falling to a rising, thereby detecting the pulse wave value $PW_i$ as a bottom value $B_i$ (Step S15).

Next, the inflection point detector 441 judges whether a relation: $PW_i > PW_{i+1}$ is satisfied (Step S16). If the relation $PW_i > PW_{i+1}$ is not satisfied (NO in Step S16), the counter "i" is incremented by one (Step S17), and the operation in Step S16 is repeated with respect to a pair of the succeeding pulse wave values on the time axis. If, on the other hand, the relation: $PW_i > PW_{i+1}$ is satisfied (YES in Step S16), the judgment result means that the pulse waveform is changed from a rising to a falling, thereby detecting the pulse wave value $PW_i$ as a peak value $P_i$ (Step S18). Then, the inflection point detector 441 confirms whether the comparison process has been completed with respect to all the data concerning the pulse waveform (Step S19). If the inflection point detector 441 judges that the comparison process has not been completed (NO in Step S19), the routine returns to Step S13, and repeats the loop from Step S13 to Step S19.

If, on the other hand, the inflection point detector 441 judges that the comparison process has been completed (YES in Step S19), the amplitude value detector 442 makes pairs with respect to the bottom value $B_i$ and the peak value $P_i$ adjacent to each other on the time axis, using the bottom value $B_i$ and the peak value $P_i$ which have been detected by the aforementioned process, and calculates a difference between the bottom value $B_i$ and the peak value $P_i$ with respect to each of the pairs to obtain the bottom-to-peak amplitude values "SW1" through "SW5" as shown in FIG. 8 (Step S20).

Thereafter, the noise remover 443 compares the first bottom-to-peak amplitude value "$SW_i$" which has been detected for the first time on the time axis by implementing the formula (1), with the second bottom-to-peak amplitude value "$SW_{i+1}$" which has been detected succeeding the first bottom-to-peak amplitude value "$SW_i$", using the bottom-to-peak amplitude values obtained in Step S20 (Step S21). Then, the noise remover 443 judges whether the formula (1) is satisfied (Step S22). If the noise remover 443 judges that the formula (1) is satisfied (YES in Step S22), the noise remover 443 judges the second bottom-to-peak amplitude value "$SW_{i+1}$" as a notch noise, and performs a marking process of erasing data corresponding to the second bottom-to-peak amplitude value "$SW_{i+1}$" (Step S23). Thereby, the bottom value and the peak value concerning the second bottom-to-peak amplitude value "$SW_{i+1}$" are no longer used in a data process to be executed thereafter. Then, the noise remover 443 decrements the count number of the peak value $P_i$ detected by the inflection point detector 441 by one in accordance with the operation in Step S23 (Step S24).

If the formula (1) is not satisfied (NO in Step S22), the noise remover 443 confirms whether the comparison process has been completed with respect to all the detected bottom-to-peak amplitude values, without recognizing the second bottom-to-peak amplitude value "$SW_{i+1}$" as a notch noise (Step S25). If the noise remover 443 judges that the comparison process has not been completed with respect to all the detected bottom-to-peak amplitude values (NO in Step S25), the counter "i" is incremented by one (Step S26), and then, the routine returns to Step S22, and repeats the loop from Step S22 to S25.

If, on the other hand, the noise remover 443 judges that the comparison process has been completed with respect to all the detected bottom-to-peak amplitude values (YES in Step S25), this means that a one-time through-process along the time axis has been completed. Then, the noise remover 443 confirms whether the count number of the peak value $P_i$ is decremented before and after the through-process (Step S27). If the noise remover 443 judges that the counter number has been decremented (YES in Step S27), the routine returns to Step S22 and repeats the loop from Step S22 to S27, because there is likelihood that the notch noises may not be completely erased. If, on the other hand, the noise remover 443 judges that the counter number has not been decremented (NO in Step S27), the noise removal process is terminated based on a judgment that all the notch noises have been erased.

The foregoing embodiment has described the arrangement, in which the relative value "a" serving as a threshold value of the amplitude value ratio used in the formula (1) for notch noise removal is set as a fixed value. Alternatively, the relative value "a" may be arbitrarily changed, i.e., changed at least once, depending on detection conditions. For instance, the preferred embodiment is, as described above referring to FIG. 10, that the relative value "a" is decreased as the number of times of repeating the through-process for notch noise removal is increased along a time axis. The reason is as follows.

Figure 15:
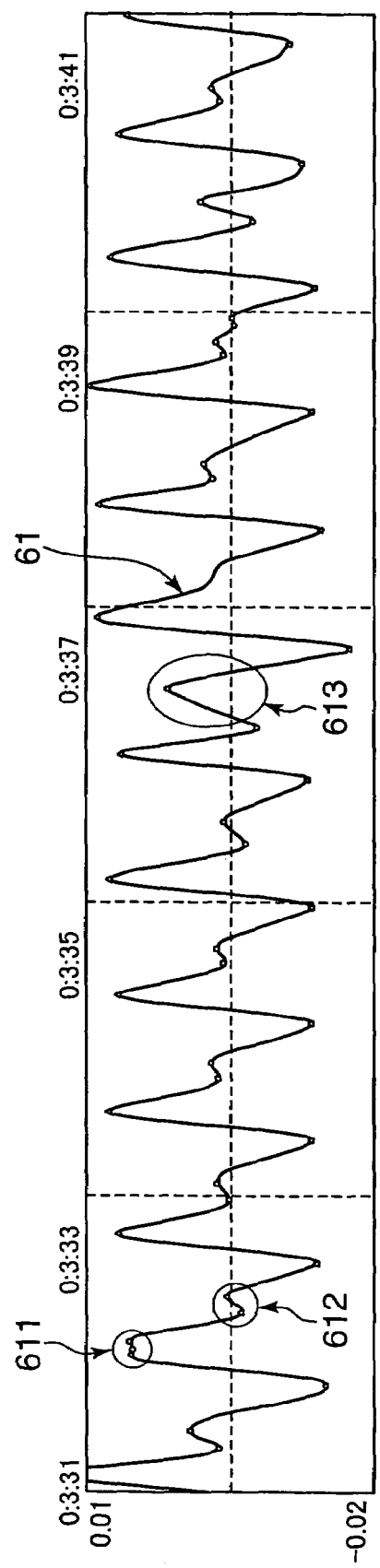
FIG. 15 is a graph showing an example of a pulse waveform.
Figure 16:
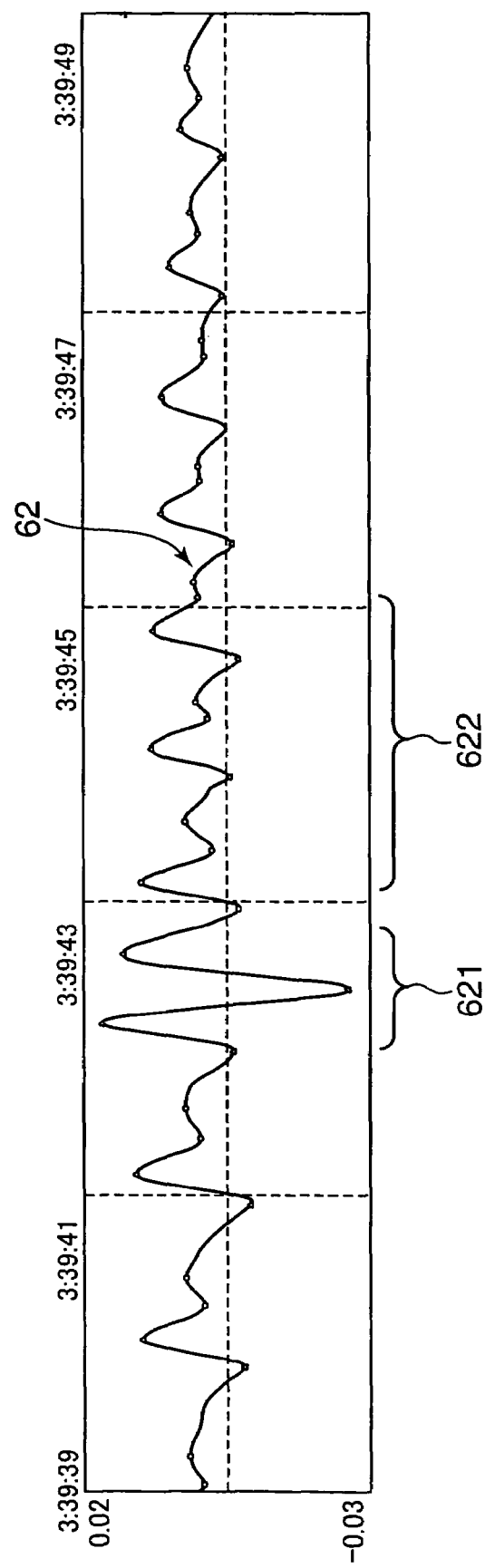
FIG. 16 is a graph showing another example of a pulse waveform.

Now, let it be assumed that a pulse waveform including pulse waveforms 61 and 62 as shown in FIGS. 15 and 16 is acquired by a one-time sequential measurement. The pulse waveform 61 shown in FIG. 15 includes small peak portions and small bottom portions corresponding to notch noises, as indicated by the numeral 611, followed by small notch noises as indicated by the numeral 612. The pulse waveform 61 also includes a notch noise indicated by the numeral 613 where a difference between a bottom value and a peak value is relatively large. On the other hand, the pulse waveform 62 shown in FIG. 16 includes a waveform portion having a significantly large amplitude in a time zone indicated by the numeral 621, followed by a waveform portion having a relatively small amplitude in a time zone indicated by the numeral 622.

In the above example, it is necessary to perform the through-process for notch noise removal at least twice in order to erase the notch noise portion as indicated by the numeral 612 in FIG. 15 where small notch noises appear sequentially (see FIG. 10). Also, it is necessary to set the relative value "a" to such a value as high as about 0.5 in order to erase the relatively large notch noise as indicated by the numeral 613.

However, in the case where the through-process for notch noise removal is repeated plural times, with the relative value "a" being set to about 0.5, the waveform portion in the time zone indicated by the numeral 622 in FIG. 16 may likely to be erased as notch noises. Specifically, the waveform portion in the time zone 622 may be recognized as a notch noise portion because of a larger relative value "a" due to accidental detection of the waveform portion having the relatively large amplitude in the time zone indicated by the numeral 621, despite the fact that the waveform portion in the time zone 622 includes peak values and bottom values that should be handled as pulse wave components.

In view of the above drawback, the through-process may preferably be repeated plural times while changing the relative value "a" to a smaller value. Specifically, the noise remover 443 shown in FIG. 5 may have a function of changing the relative value "a", and the through-process for notch noise removal at the n-th time may be executed by reducing the relative value "a" depending on detection conditions. For instance, in the case where the pulse waveforms 61 and 62 as shown in FIGS. 15 and 16 are supposed to appear, the notch noise removal process is executed twice to erase relatively large notch noises by setting the relative value "a" to 0.5, and then, the notch noise removal process is repeated a certain number of times until relatively small notch noises are erased by setting the relative value "a" to 0.1. Alternatively, the relative value "a" may be gradually decreased as the number of times of repeating the through-process is increased, or the relative value "a" may be decreased stepwise in the order of about two to four times. Changing the relative value "a" as mentioned above enables to thoroughly erase the small notch noises while securely erasing the large notch noises without erasing the waveform portion which should be handled as a pulse wave component.

Figure 17:
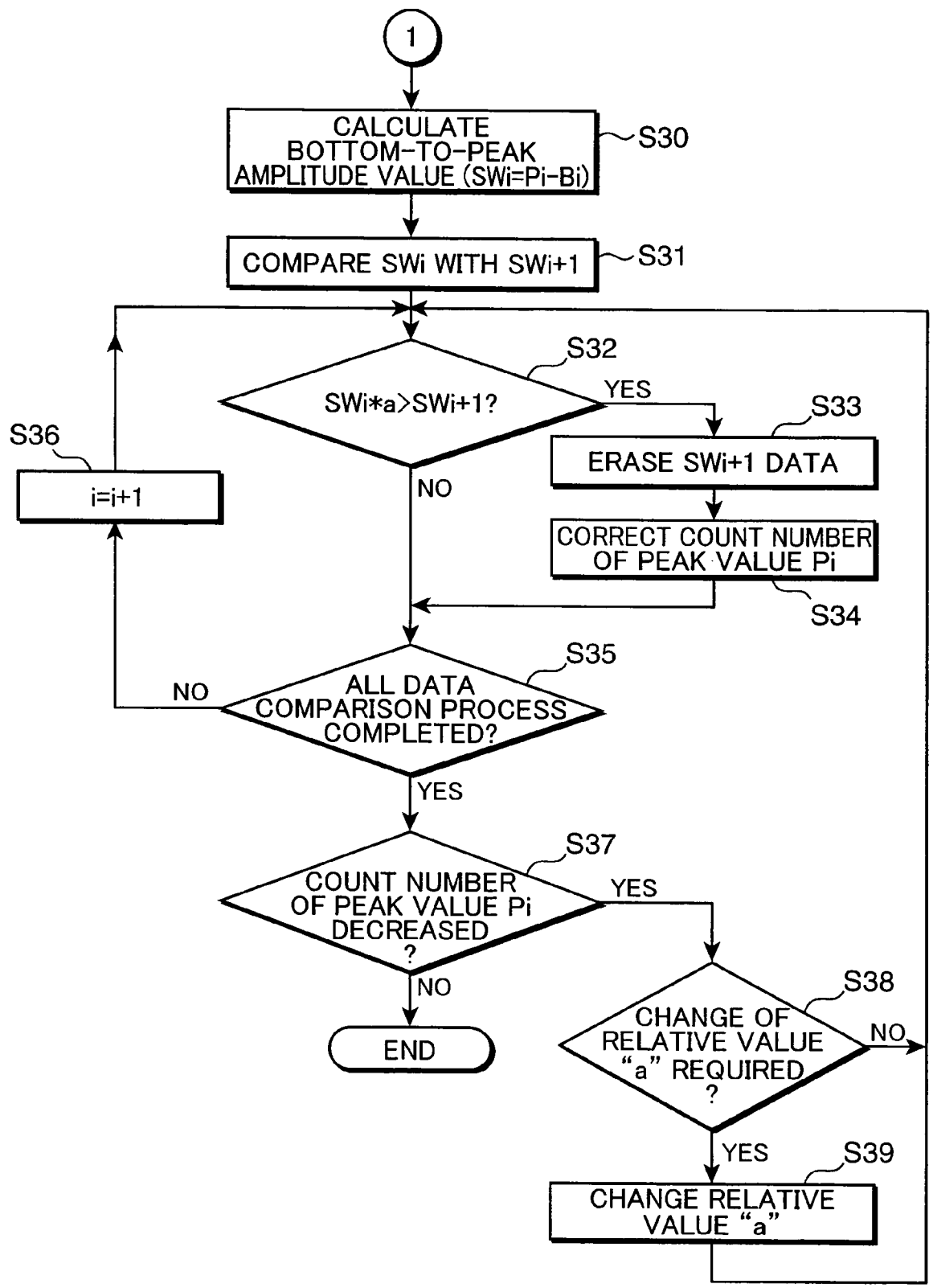
FIG. 17 is a flowchart showing a process operation in an arrangement that a noise remover has a function of changing a relative value "a".

FIG. 17 is a flowchart showing a process operation in the case where the noise remover 443 has a function of changing the relative value "a". Since Steps S30 through S36 in FIG. 17 are substantially identical to Steps S20 through S26 described referring to the flowchart of FIG. 14, description thereof will be omitted herein.

After completion of a comparison process with respect to all the data in the pulse waveform (YES in Step S35), the noise remover 443 judges whether the count number of the peak value $P_i$ has been decreased before and after the through-process (Step S37). If the noise remover 443 judges that the count number has been decreased (YES in Step S37), it is judged whether it is necessary to change the relative value "a" from a default to a certain value before the routine returns to Step S32 to repeat the loop from Step S32 to S37 (Step S38).

If it is judged that change of the relative value "a" is necessary (YES in Step S38) the noise remover 443 changes the relative value "a" to a certain value (Step S39). If the relative value is set as mentioned above, the relative value "a" is changed from 0.5 to 0.1 in executing the third-time through-process. Thereafter, the routine returns to Step S32 to repeat the loop from Step S32 to Step S37. If, on the other hand, the noise remover 443 judges that change of the relative value "a" is not necessary (NO in Step S38), the routine returns to Step S32 without changing the relative value "a", and repeats the loop from Step S32 to Step S37. If, on the other hand, it is judged that the count number has not been decreased in Step S37 (NO in Step S37), the noise removal process is terminated based on a judgment that all the notch noises have been erased.

The invention has been described by way of the foregoing embodiment. Alternatively, the following modifications may be applied to the invention.

(I) In the foregoing embodiment, the noise remover 443 compares the two bottom-to-peak amplitude values adjacent to each other on the time axis, and judges whether a ratio of the succeeding bottom-to-peak amplitude value to the preceding bottom-to-peak amplitude value is smaller than a predetermined value. Alternatively, two bottom-to peak amplitude values that are not adjacent to each other on the time axis, or more than two bottom-to-peak amplitude values may be compared.

(II) In the foregoing embodiment, the through-process is repeated until decrease of the count number of the peak value $P_i$ is not detected before and after the through-process. Alternatively, the number of times of repeating the through-process may be fixed to a predetermined value e.g. 5 times. In the altered arrangement, the relative value "a" may be changed in the course of the through-processes. For instance, the through-process is conducted twice, with the relative value "a" being set to 0.5, and then, the through-process is conducted three times, with the relative value "a" being set to 0.1.

(III) A case discriminator may be provided so that patterns concerning pulse wave peak-to-peak intervals including the exemplified pattern shown in FIG. 11 may be classified according to cases of a disease; the classified patterns may be stored in the storage 25 or a like device as discrimination indexes; and the data analyzer 42 may compare pulse wave peak-to-peak intervals actually obtained by the interval calculator 45 with the classified patterns to approximately determine the case of the disease to which the actually obtained pattern belongs.

(IV) In the foregoing embodiment, the pulse wave data measured by the sensing section 23 is temporarily stored in the storage 25, and the stored pulse wave data is analyzed by the data analyzer 42 afterwards. Alternatively, the pulse wave data may be sequentially analyzed, and pulse wave information obtained by the sequential analysis may be displayed on the display device 212 as a live indication. Further alternatively, an arrhythmia alert lamp or a like device may be provided, and in the case where regularities of the pulse wave peak-to-peak intervals are fluctuated over a predetermined threshold value, the arrhythmia alert lamp or the like device may be ignited based on an assumption that an arrhythmia has occurred in the subject. Furthermore alternatively, generation of an arrhythmia may be radioed to a medical institute, a nurse center, or a like site, in place of igniting the alert lamp. Furthermore alternatively, the number of occurrences of an arrhythmia or the kind of the arrhythmia may be displayed on the display device 212.

(V) In the foregoing embodiment, the interval calculator 45 calculates pulse wave peak-to-peak intervals or pulse wave bottom-to-bottom intervals corresponding to electrocardiogram RR-intervals with respect to the pulse waveform after noise removal. Alternatively, differences each between a peak value and a bottom value adjacent to each other on the time axis may be obtained as peak-to-bottom amplitudes in addition to or in place of the pulse wave peak-to-peak intervals or the pulse wave bottom-to-bottom intervals. For instance, the amplitude value detector 442 as an amplitude value calculator may obtain an amplitude based on the bottom value "B1" and the peak value "P1", an amplitude based on the bottom value "B3" and the peak value "P3", an amplitude based on the bottom value "B5" and the peak value "P5", and amplitudes based on the rest of the peak values and the rest of the bottom values with respect to the pulse waveform 52 after the notch noise removal shown in FIG. 9, as diagnostic information.

For example, amplitudes between the peak values and the bottom values fluctuate as well as electrocardiogram RR-intervals i.e. pulse wave peak-to-peak intervals in atrial fibrillation patients. Accordingly, the atrial fibrillation patients can be diagnosed by obtaining pulse wave peak-to-peak intervals and amplitudes between peak values and bottom values, and by assessing the fluctuations thereof.

Also, when the sympathetic nerve acts, a blood vessel shrinks, and amplitudes between peak values and bottom values are decreased. This means that smaller amplitudes of peak/bottom values than a normal pulsation amplitude show that the sympathetic nerve acts effectively. Accordingly, autonomic nerve disorder or a like symptom can be diagnosed by detecting the amplitudes between peak values and bottom values. Also, it is possible to assess a peripheral circulatory disorder based on the amplitudes of a pulse wave.

Figure 18:
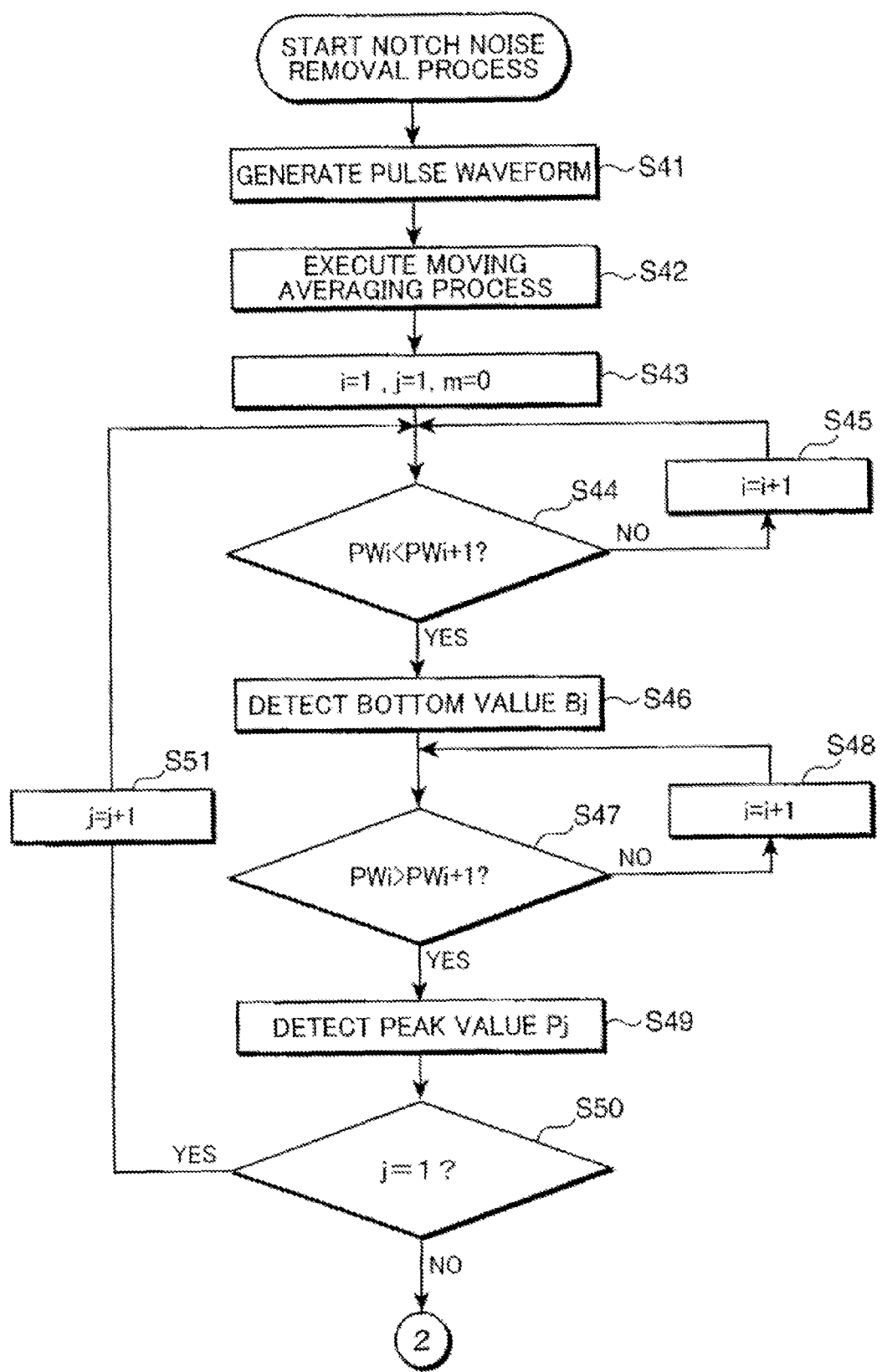
FIGS. 18 and 19 are flowcharts showing a detailed flow on an altered notch noise removal process.
Figure 19:
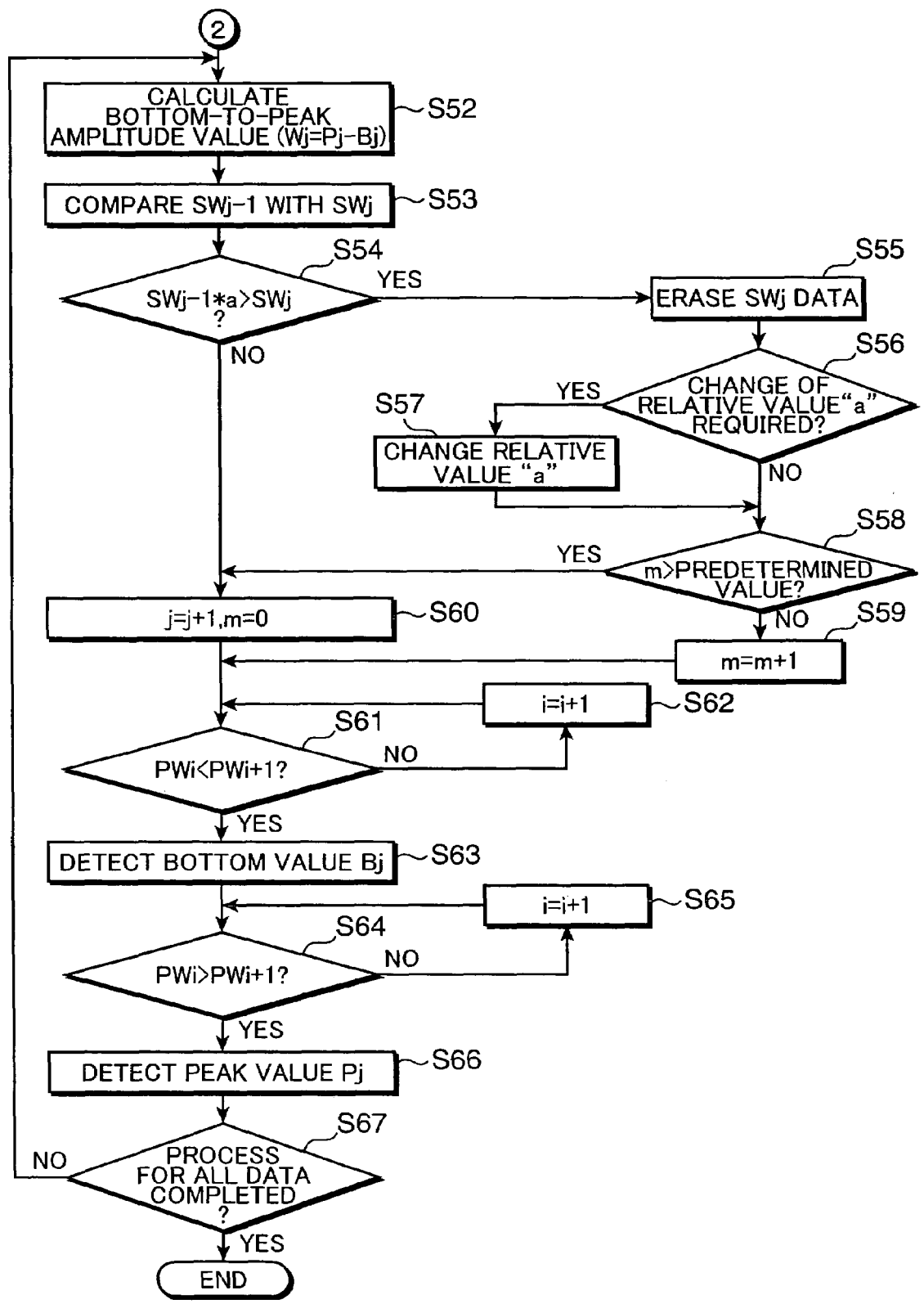
Figure 20:
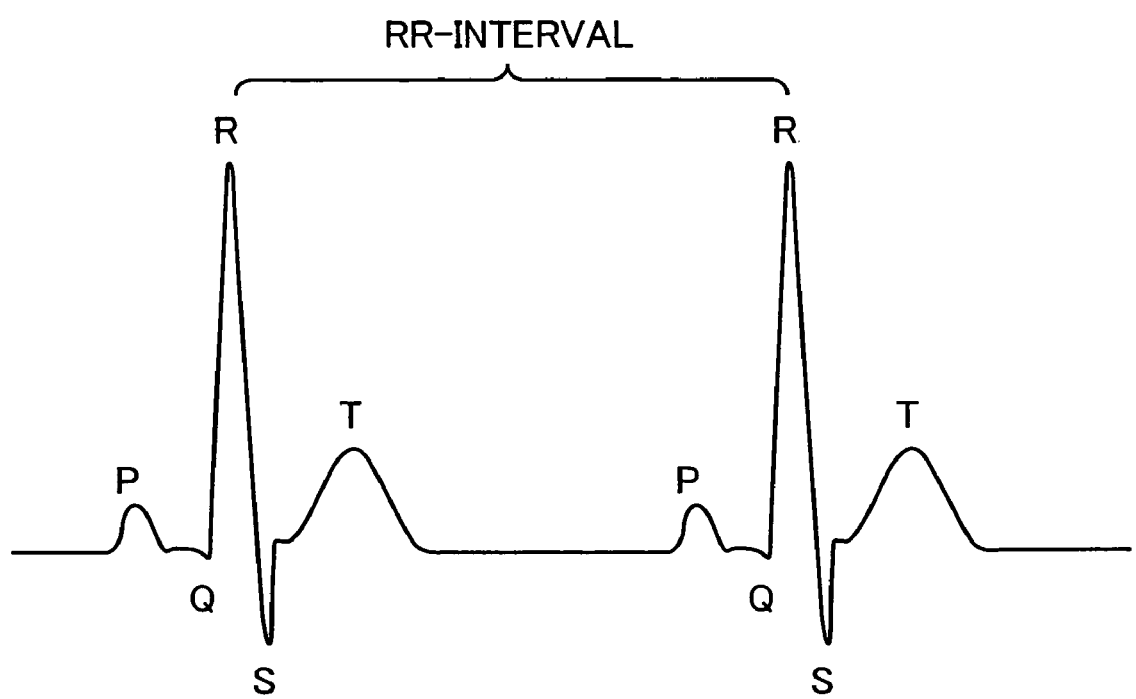
FIG. 20 is a graph showing a waveform in an electrocardiogram, and electrocardiogram RR-intervals.

(VI) In the foregoing embodiment, the through-process is executed, using all the measurement data. Alternatively, pulse wave peak-to-peak intervals may be calculated, while removing notches on a real-time basis. FIGS. 18 and 19 are flowcharts showing a case of calculating pulse wave peak-to-peak intervals while removing notches on a real-time basis. Similarly to the description referring to the flowchart of FIG. 13, a pulse waveform is generated (Step S41), and the pulse waveform is smoothed (Step S42). Then, counters are set to: i=1, j=1, and m=0 (S43).

Next, the inflection point detector 441 of the noise removal processor 44 judge whether a relation: $PW_i < PW_{i+1}$ is satisfied (Step S44). If the relation: $PW_i < PW_{i+1}$ is not satisfied (NO in Step S44), the counter "i" is incremented by one (Step S45), and the operation in Step S44 is repeated. If, on the other hand, the relation: $PW_i < PW_{i+1}$ is satisfied (YES in Step S44), the pulse wave value $PW_i$ is detected as a bottom value $B_i$ (Step S46).

Next, the inflection point detector 441 judges whether a relation: $PW_i > PW_{i+1}$ is satisfied (Step S47). If the relation $PW_i > PW_{i+1}$ is not satisfied (NO in Step S47), the counter "i" is incremented by one (Step S48), and the operation in Step S47 is repeated. If, on the other hand, the relation: $PW_i > PW_{i+1}$ is satisfied (YES in Step S47), the pulse wave value $PW_i$ is detected as a peak value $P_i$ (Step S49). Then, it is judged whether the counter j=1 (Step S50). If it is judged that the counter j=1 (YES in Step S50), the counter "j" is incremented by one (Step S51), and the routine returns to Step S44, and repeats the loop from Step S44 to Step S50. If, on the other hand, it is not judged that the counter j=1 (NO in Step S50), the routine proceeds to the flow in FIG. 19.

Referring to FIG. 19, the amplitude value detector 442 calculates a difference between the bottom value $B_j$ and the peak value $P_j$ which are detected to be adjacent to each other on the time axis to obtain a bottom-to-peak amplitude value $SW_j$ (Step S52). Thereafter, the noise remover 443 compares the bottom-to-peak amplitude value $SW_j$ obtained in Step S52 with the bottom-to-peak amplitude value $SW_{j-1}$ obtained in the previous notch removal process as a reference amplitude value $SW_{j-1}$ (Step S53).

Then, it is judged whether the relation: $SW_{j-1} * a > SW_j$ is satisfied (Step S54). If it is judged that the relation is satisfied (YES in Step S54), the noise remover 443 determines the $SW_j$ as a notch noise, and erases the data concerning the $SW_j$ (Step S55). If, on the other hand, it is not judged that the relation is satisfied (NO in Step S54), the currently obtained $SW_j$ is set as a reference amplitude value for a bottom-to-peak amplitude value to be obtained in a next notch removal process. Then, the counter "j" is incremented by one (Step S60), and the routine executes a process of obtaining a succeeding bottom value $B_j$ and a succeeding peak value $P_j$ on the time axis by executing operations identical to the operations in Steps S44 through S49 (Steps S61 through S66).

After the operation in Step S55, it is judged whether the relative value "a" is to be changed (Step S56). If the change is scheduled (YES in Step S56), the relative value "a" is changed (Step S57). This is to thoroughly erase the small notch noises while securely erasing the large notch noises without erasing the waveform portion which should be handled as a pulse wave component, as mentioned above. Then, it is judged whether the number "m" of times of repeating the amplitude value comparison concerning the same pulse wave data has exceeded a predetermined value e.g. 5 times (Step S58). This operation corresponds to the process described in the modification (II). If the number "m" has exceeded the predetermined value (YES in Step S58), the routine proceeds to Step S60, and at this time, the relative value "a" is defaulted. If, on the other hand, the number "m" does not exceed the predetermined value (NO in Step S58), the counter "m" is incremented by one (Step S59), and the routine proceeds to Step S61.

After the operation in Step S66, it is judged whether the process concerning all the measurement data has been completed (Step S67). If it is judged that the process has not been completed (NO in Step S67), the routine returns to Step S52, and repeats the loop from Step S52 to Step S67. Specifically, the bottom-to-peak amplitude value comparison process is repeated while successively updating the reference amplitude value. If, on the other hand, it is judged that the process concerning all the measurement data has been completed (YES in Step S67), the routine is ended. Executing the real-time notch noise removal process as mentioned above enables to calculate pulse wave peak-to-peak intervals on a real-time basis.

(VII) It is possible to provide an operation program of executing a process to be implemented by the pulse wave data analyzing system "S0" or a like system, as a modified embodiment to carry out the invention, in place of the pulse wave data analyzing system "S0" i.e. the pulse wave measuring device 20 or a like device. The program may be provided as a program product by recording the program in a computer-readable recording medium, which is an attachment to a computer, such as a flexible disk, a CD-ROM, an ROM, an RAM, or a memory card. Also, the program may be provided by downloading via a network.

In general, the routines executed to implement the embodiment of the invention, whether implemented as part of an operating system or a specific application, component, program, object, module or sequence of instructions will be referred to as "programs". The program comprises one or more instructions that are resident at various times in various memory and storage devices in a computer, and that cause the computer to perform the steps necessary to execute steps or elements embodying the various aspects of the invention.

The embodiment of the invention has and will be described in the context of functioning the computer and computer system. However, those skilled in the art will appreciate that various embodiments of the invention are capable of being distributed as a program product in a variety of forms, and that the invention applies equally regardless of the particular type of signal bearing media used to actually carry out the distribution. Examples of signal bearing media include but are not limited to recordable type media such as volatile and non-volatile memory devices, floppy and other removable disks, hard disk drives, optical disks (e.g., CD-ROM's, DVD's, etc.), among others, and transmission type media such as digital and analog communication links, including the Internet.

The following is a brief description on the embodiments.

An aspect of the invention is directed to a pulse wave data analyzing method for extracting vital information out of pulse wave data concerning a living body. The method comprises a noise removal step of: detecting bottom values and peak values along a time axis in a time-series manner out of pulse wave data obtained by sequentially measuring a pulse wave of a subject for a predetermined period; making pairs with respect to the bottom values and the peak values adjacent to each other on the time axis to obtain bottom-to-peak amplitude values along the time axis, the bottom-to-peak amplitude value being a difference between the bottom value and the peak value in each of the pairs; and comparing each set of the two bottom-to-peak amplitude values adjacent to each other along the time axis to remove the bottom value and the peak value relating to the smaller bottom-to-peak amplitude value in the each set as a noise, if a ratio of the one of the two bottom-to-peak amplitude values to the other one of the two bottom-to-peak amplitude values is larger than a predetermined value.

In the above arrangement, a comparison is made concerning the each set of the two bottom-to-peak amplitude values adjacent to each other along the time axis, which are obtained based on the pairs of the bottom values and the peak values adjacent to each other out of the pulse wave data. If the amplitude value ratio is larger than the predetermined value, in other words, if the one of the two bottom-to-peak amplitude values is smaller than the other one of the two bottom-to-peak amplitude values with respect to a predetermined relative value, the bottom value and the peak value relating to the smaller bottom-to-peak amplitude value are removed as the noise. Generally, a bottom-to-peak amplitude value corresponding to a notch is equal to or smaller than a bottom-to-peak amplitude value which should be handled as a pulse wave component. Accordingly, the bottom-to-peak amplitude value corresponding to the notch results in a small amplitude value. This arrangement enables to accurately obtain peak-to-peak intervals or bottom-to-bottom intervals by removing the smaller bottom-to-peak amplitude value as a notch noise if the amplitude value ratio is larger than the predetermined value.

According to the above arrangement, the bottom-to-peak amplitude values adjacent to each other on the time axis are compared to remove the bottom value and the peak value relating to the bottom-to-peak amplitude value which is smaller than the predetermined value. This enables to securely remove the noises irrespective of the frequency of the pulse wave or the waveform configuration. Accordingly, notch portions included in the pulse wave data can be securely removed to obtain accurate pulse wave data concerning the living body, which allows medical staffs or a like person to accurately make various diagnoses based on the pulse wave data.

Preferably, the pulse wave data analyzing method may further comprise a step of obtaining peak-to-peak intervals or bottom-to-bottom intervals corresponding to electrocardiogram RR-intervals based on pulse wave data obtained by executing the noise removal step. In this arrangement, since the peak-to-peak intervals or the bottom-to-bottom intervals can be obtained based on the pulse wave data obtained by executing the noise removal step, a diagnosis concerning an arrhythmia or a like symptom can be accurately made.

According to the above arrangement, even in the case where an arrhythmia or a like symptom has occurred in the subject, the notch portions included in the pulse wave data can be securely removed to accurately detect peak portions. This enables to detect pulse wave peak-to-peak intervals having a high correlation to RR-intervals obtained based on an electrocardiogram. This allows for accurate detection of the arrhythmia without using a holter monitor which is stressful to the subject, and enables to recognize a disease at an early stage thereof. Also, the pulse wave measurement is a simple measurement method, which is easily conducted even for elderly people. Accordingly, the pulse wave measurement can be utilized for screening symptoms such as an atrial fibrillation with a high incidence rate among the elderly people at an early stage thereof. Further, since the pulse wave measurement is less burdensome to the subject, the arrangement is advantageous in performing a long time continuous measurement required in confirming the efficacy of a drug. For instance, it is necessary to confirm that an atrial fibrillation has not occurred for about two weeks to determine that the atrial fibrillation has completely been eliminated.

Preferably, the pulse wave data analyzing method may further comprise a step of obtaining bottom-to-peak amplitude values based on pulse wave data obtained by executing the noise removal step. In this arrangement, various diagnoses such as a diagnosis concerning the sympathetic nerve activity can be made by utilizing the bottom-to-peak amplitude values.

The above arrangement enables to perform the diagnoses in a wider range by utilizing the bottom-to-peak amplitude values, thereby enhancing usability of the inventive method.

Preferably, the pulse wave data analyzing method may further comprise a step of executing a moving averaging process with respect to the pulse wave data prior to detecting the bottom values and the peak values out of the pulse wave data. In this arrangement, pulse wave data fluctuations, which are frequently detected in raw pulse wave data within a small measurement duration, and are likely to be regarded as bottom values or peak values, can be smoothed by the moving averaging process, thereby simplifying the process of extracting the bottom values and the peak values.

The above arrangement enables to simplify the process of extracting the bottom values and the peak values by executing the moving averaging process, which resultantly expedites the data analyzing process.

Preferably, in any one of the above arrangements, the noise removal step may be executed one or more times with respect to pulse wave data obtained by executing the noise removal step for the first time. In this arrangement, even if the pulse wave data includes a number of notch noises in amplitudes of the pulse waveform, the notch noises can be securely removed, thereby enabling to accurately determine the positions of the bottom values and the peak values. This enables to provide medical staffs or a like person with more accurate pulse wave interval data.

Preferably, in the above arrangement, a threshold value of the amplitude value ratio used in judging whether the bottom value and the peak value are to be removed as the noise may be changed at least once in repeating the noise removal step. This arrangement enables to securely remove the notch noises depending on detection conditions. For instance, notch noises including notch noises with a relatively large amplitude and notch noises with a relatively small amplitude can be successively and securely removed by decreasing the threshold value of the amplitude value ratio as the number of times of repeating the noise removal step is increased.

The above arrangement enables to thoroughly remove the small notch noises while securely removing the large notch noises without erasing the pulse wave interval data which should be handled as a pulse wave component.

Another aspect of the invention is directed to a pulse wave data analyzing system for extracting vital information out of pulse wave data concerning a living body. The system comprises: a pulse wave detector for obtaining pulse wave information concerning a subject at a predetermined sampling frequency to acquire pulse wave data in association with a time axis; and a data analyzer for executing a noise removal process to analyze the pulse wave data. The data analyzer includes: an inflection point detector for detecting bottom values and peak values along the time axis in a time-series manner out of the pulse wave data; an amplitude value detector for making pairs with respect to the bottom values and the peak values adjacent to each other on the time axis to obtain bottom-to-peak amplitude values along the time axis, the bottom-to-peak amplitude value being a difference between the bottom value and the peak value in each of the pairs; and a noise remover for comparing each set of the two bottom-to-peak amplitude values adjacent to each other along the time axis to remove the bottom value and the peak value relating to the smaller bottom-to-peak amplitude value in the each set as a noise, if a ratio of the one of the two bottom-to-peak amplitude values to the other one of the two bottom-to-peak amplitude values is larger than a predetermined value.

In the above arrangement, the inflection point detector of the data analyzer obtains the bottom values and the peak values based on the pulse wave data obtained by the pulse wave detector. The amplitude value detector makes the pairs with respect to the bottom values and the peak values adjacent to each other on the time axis to obtain the bottom-to-peak amplitude values. The noise remover compares the each set of the two bottom-to-peak amplitude values adjacent to each other along the time axis to remove the bottom value and the peak value relating to the smaller bottom-to-peak amplitude value in the each set, as the noise, if the ratio of the one of the two bottom-to-peak amplitude values to the other one of the two bottom-to-peak amplitude values is larger than the predetermined value.

Preferably, the data analyzer may include an interval calculator for obtaining peak-to-peak intervals or bottom-to-bottom intervals corresponding to electrocardiogram RR-intervals based on pulse wave data obtained by the noise removal by the noise remover. In this arrangement, the interval calculator obtains the peak-to-peak intervals or the bottom-to-bottom intervals based on the pulse wave data obtained by executing the noise removal by the noise remover. This enables to detect pulse wave peak-to-peak intervals having a high correlation to the electrocardiogram RR-intervals, as compared with an arrangement of obtaining peak-to-peak intervals or bottom-to-bottom intervals based on raw pulse wave data, because the notch noises have been removed.

Preferably, the data analyzer may include an amplitude value calculator for obtaining bottom-to-peak amplitude values, as diagnostic information, based on pulse wave data obtained by executing the noise removal by the noise remover. In this arrangement, various diagnoses such as a diagnosis concerning the sympathetic nerve activity can be made, utilizing the bottom-to-peak amplitude values obtained by the amplitude value calculator.

Preferably, the data analyzer may include a moving averaging processor for executing a moving averaging process with respect to the pulse wave data obtained by the pulse wave detector. In this arrangement, the moving averaging processor smoothes fluctuations of the pulse wave data, thereby simplifying the process of extracting the bottom values and the peak values.

Preferably, in any one of the above arrangements, the data analyzer may control the inflection point detector, the amplitude value detector, and the noise remover to execute the noise removal process one or more times with respect to pulse wave data obtained by executing the noise removal process for the first time. In this arrangement, even if the pulse wave data includes a number of notch noises in amplitudes of the pulse wave, the notch noises can be securely removed, thereby enabling to accurately determine the positions of the bottom values and the peak values.

Preferably, the noise remover may change a threshold value of the amplitude value ratio used in judging whether the bottom value and the peak value are to be removed as the noise at least once in repeating the noise removal process. This arrangement enables to securely remove the notch noises depending on detection conditions. For instance, notch noises including notch noises with a relatively large amplitude and notch noises with a relatively small amplitude can be successively and securely removed by decreasing the threshold value of the amplitude value ratio set by the noise remover, as the number of times of repeating the noise removal step is increased.

Preferably, in any one of the above arrangements, the pulse wave data analyzing system may further comprise a display section for displaying a data analysis result by the data analyzer, wherein the pulse wave detector, the data analyzer, and the display section are mounted on a device removably attachable to the subject. This arrangement enables to realize the inventive pulse wave data analyzing system as a single device where all the necessary functions for the pulse wave data analysis are loaded, and which is wearable to the subject. Thus, a compact system with enhanced portability is provided.

Preferably, in any one of the above arrangements, the pulse wave data analyzing system may further comprises: a storage section for storing therein the pulse wave data obtained by the pulse wave detector; a first device including the pulse wave detector and the storage section, the first device being removably attachable to the subject; and a second device including the data analyzer, the second device being communicable with the first device to acquire the pulse wave data stored in the storage section. In this arrangement, the first device for acquiring the pulse wave data, and the second device e.g. a personal computer for executing the data analysis as individual parts constitute the inventive pulse wave data analyzing system.

The above arrangement enables to enhance wearabiliy by constructing the first device to be removably attached to the subject into a simplified arrangement, and to perform enhanced data analysis by using a personal computer or a like device as the second device.

Preferably, the data analyzer may analyze the pulse wave data on a real-time basis, and controls a display section to display the pulse wave information obtained by the analysis thereof. This arrangement allows the user to confirm the pulse wave information on the display section on the real-time basis, thereby enhancing usability of the system.

Preferably, the data analyzer may include a storage section for storing the analyzed pulse wave information therein. Since the analyzed pulse wave information can be stored as data, confirmation on the pulse wave information which is executed after the measurement, or a statistical processing can be facilitated.

Yet another aspect of the invention is directed to a pulse wave data analyzing program product for extracting vital information out of pulse wave data concerning a living body. The program product comprises: a program which causes a data analyzer for analyzing the pulse wave data to execute: a readout step of obtaining pulse wave information concerning a subject at a predetermined sampling frequency to acquire pulse wave data in association with a time axis; a detection step of detecting bottom values and peak values along a time axis in a time-series manner out of the pulse wave data; an acquisition step of making pairs with respect to the bottom values and the peak values adjacent to each other on the time axis to obtain bottom-to-peak amplitude values along the time axis, the bottom-to-peak amplitude value being a difference between the bottom value and the peak value in each of the pairs; and a noise removal step of comparing each set of the two bottom-to-peak amplitude values adjacent to each other along the time axis to remove the bottom value and the peak value relating to the smaller bottom-to-peak amplitude value in the each set as a noise, if a ratio of the one of the two bottom-to-peak amplitude values to the other one of the two bottom-to-peak amplitude values is larger than a predetermined value; and a signal bearing media bearing the program.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A method for operating a pulse wave data analyzer to extract vital information out of pulse wave data concerning a living body, the pulse wave data analyzer comprising a central processing unit and a digital signal processor, the method for operating comprising the steps of:

employing the pulse wave data analyzer to execute a noise removal step including:
detecting bottom values and peak values along a time axis in a time-series manner out of pulse wave data obtained by sequentially measuring a pulse wave of a subject for a predetermined period;

making pairs with respect to the bottom values and the peak values adjacent to each other on the time axis to obtain bottom-to-peak amplitude values along the time axis, the bottom-to-peak amplitude values being a difference between the bottom value and the peak value in each of the pairs; and comparing each set of two bottom-to-peak amplitude values adjacent to each other along the time axis to remove the bottom value and the peak value relating to the smaller bottom-to-peak amplitude value in each set as noise, if a ratio of one of the two bottom-to-peak amplitude values to the other one of the two bottom-to-peak amplitude values is larger than a predetermined value;

employing the pulse wave data analyzer to obtaining peak-to-peak intervals or bottom-to-bottom intervals corresponding to electrocardiogram RR-intervals based on pulse wave data obtained by executing the noise removal step; and employing the pulse wave data analyzer to output the peak-to-peak intervals or bottom-to-bottom intervals.

2. The method of operating a pulse wave data analyzer according to claim 1, further comprising a step of:
obtaining bottom-to-peak amplitude values based on pulse wave data obtained by executing the noise removal step.

3. The method of operating a pulse wave data analyzer according to claim 1, further comprising a step of:
executing a moving averaging process with respect to the pulse wave data prior to detecting the bottom values and the peak values out of the pulse wave data.

4. The method of operating a pulse wave data analyzer according to claim 1,
wherein the noise removal step is executed one or more times with respect to pulse wave data obtained by executing the noise removal step for the first time.

5. The method of operating a pulse wave data analyzer according to claim 4,
wherein, when the noise removal step is executed more than one time, a threshold value of the amplitude value ratio used in judging whether the bottom value and the peak value are to be removed as noise is changed at least once in repeating the noise removal step.

6. A pulse wave data analyzing system for extracting vital information out of pulse wave data concerning a living body, the system comprising:
a pulse wave detector for obtaining pulse wave information concerning a subject at a predetermined sampling frequency to acquire pulse wave data in association with a time axis; and
a data analyzer for executing a noise removal process to analyze the pulse wave data,
the data analyzer including:
an inflection point detector for detecting bottom values and peak values along the time axis in a time-series manner out of the pulse wave data,
an amplitude value detector for making pairs with respect to the bottom values and the peak values adjacent to each other on the time axis to obtain bottom-to-peak amplitude values along the time axis, the bottom-to-peak amplitude values being a difference between the bottom value and the peak value in each of the pairs,
a noise remover for comparing each set of two bottom-to-peak amplitude values adjacent to each other along the time axis to remove the bottom value and the peak value relating to the smaller bottom-to-peak amplitude value in each set as noise, if a ratio of one of the two bottom-to-peak amplitude values to the other one of the two bottom-to-peak amplitude values is larger than a predetermined value, and an interval calculator for obtaining peak-to-peak intervals or bottom-to-bottom intervals corresponding to electrocardiogram RR-intervals based on pulse wave data obtained by executing the noise removal by the noise remover.

7. The pulse wave data analyzing system according to claim 6, wherein
the data analyzer includes an amplitude value calculator for obtaining bottom-to-peak amplitude values, as diagnostic information, based on pulse wave data obtained by executing the noise removal by the noise remover.

8. The pulse wave data analyzing system according to claim 6, wherein
the data analyzer includes a moving averaging processor for executing a moving averaging process with respect to the pulse wave data obtained by the pulse wave detector.

9. The pulse wave data analyzing system according to claim 6, wherein
the data analyzer is adapted to control the inflection point detector, the amplitude value detector, and the noise remover to execute the noise removal process one or more times with respect to pulse wave data obtained by executing the noise removal process for the first time.

10. The pulse wave data analyzing system according to claim 9, wherein
the noise remover is adapted to change a threshold value of the amplitude value ratio used in judging whether the bottom value and the peak value are to be removed as noise at least once when the noise removal process is executed more than one time.

11. The pulse wave data analyzing system according to claim 6, further comprising:
a display section for displaying a data analysis result by the data analyzer, wherein
the pulse wave detector, the data analyzer, and the display section are mounted on a device removably attachable to the subject.

12. The pulse wave data analyzing system according to claim 6, further comprising:
a storage section for storing therein the pulse wave data obtained by the pulse wave detector;
a first device including the pulse wave detector and the storage section, the first device being removably attachable to the subject; and
a second device including the data analyzer, wherein the second device is adapted to communicate with the first device to acquire the pulse wave data stored in the storage section.

13. The pulse wave data analyzing system according to claim 6, wherein
the data analyzer is adapted to analyze the pulse wave data on a real-time basis, and control a display section to display analyzed pulse wave information.

14. The pulse wave data analyzing system according to claim 6, wherein
the data analyzer includes a storage section for storing the analyzed pulse wave information therein.

15. A pulse wave data analyzing program product for extracting vital information out of pulse wave data concerning a living body, the program product comprising:
a program which causes a data analyzer for analyzing the pulse wave data to execute steps for:
obtaining pulse wave information concerning a subject at a predetermined sampling frequency to acquire pulse wave data in association with a time axis;

detecting bottom values and peak values along the time axis in a time-series manner out of the pulse wave data;

making pairs with respect to the bottom values and the peak values adjacent to each other on the time axis to obtain bottom-to-peak amplitude values along the time axis, the bottom-to-peak amplitude values being a difference between the bottom value and the peak value in each of the pairs; and comparing each set of two bottom-to-peak amplitude values adjacent to each other along the time axis to remove the bottom value and the peak value relating to the smaller bottom-to-peak amplitude value in each set as noise, if a ratio of one of the two bottom-to-peak amplitude values to the other one of the two bottom-to-peak amplitude values is larger than a predetermined value;

obtaining peak-to-peak intervals or bottom-to-bottom intervals corresponding to electrocardiogram RR-intervals based on the pulse wave data from which noise has been removed; and a signal bearing media bearing the program.

16. A pulse wave data analyzing system for extracting vital information out of pulse wave data concerning a living body, the system comprising:

a pulse wave detector for obtaining pulse wave data in association with a time axis; and a data analyzer for analyzing and removing noise from the pulse wave data, the data analyzer including:

an inflection point detector adapted to detect bottom values and peak values along the time axis in a time-series manner out of the pulse wave data, an amplitude value detector adapted to identify pairs of bottom values and peak values adjacent to each other on the time axis and calculate bottom-to-peak amplitude values along the time axis, the bottom-to-peak amplitude values being a difference between the bottom value and the peak value in each of the pairs of bottom values and peak values, a noise remover adapted to calculate a ratio between each set of bottom-to-peak amplitude values adjacent to each other along the time axis and removing the bottom value and the peak value corresponding to the smaller bottom-to-peak amplitude value of each set as noise, if the ratio is larger than a predetermined value, and an interval calculator adapted to obtain peak-to-peak intervals or bottom-to-bottom intervals corresponding to electrocardiogram RR-intervals based on pulse wave data from which noise has been removed by the noise remover.

* * * * *